United States Patent [19]

Kilbourn et al.

[11] 4,241,079

[45] Dec. 23, 1980

[54] 2-IMINO SUBSTITUTED ISOTHIOUREIDOBENZENE

[75] Inventors: Edward E. Kilbourn, Chalfont; W. David Weir, Levittown, both of Pa.

[73] Assignee: Rohm and Haas Company, Philadelphia, Pa.

[21] Appl. No.: 902,623

[22] Filed: May 4, 1978

[51] Int. Cl.$^3$ .................... A01N 9/14; C07D 149/243
[52] U.S. Cl. ........................... 424/285; 260/326 S; 260/347.2; 260/456 A; 260/465 D; 424/251; 424/263; 424/269; 424/270; 424/272; 424/273 R; 424/274; 424/275; 424/282; 424/300; 542/422; 542/423; 544/316; 546/273; 546/291; 546/328; 548/187; 549/59; 549/65; 549/72

[58] Field of Search ............... 260/326 S, 454, 465 D, 260/456 A, 347.2; 424/251, 263, 269, 270, 272, 274, 275, 285, 300, 273 R, 282; 542/423, 422; 560/13, 16, 10; 549/59, 65, 72; 546/273, 291, 328; 544/316; 548/187

[56] References Cited

U.S. PATENT DOCUMENTS 3,860,586  1/1975  Kilbourn et al. .................... 542/423

*Primary Examiner*—Richard Raymond
*Attorney, Agent, or Firm*—Terence P. Strobaugh

[57] ABSTRACT

2-Imino substituted isothioureidobenzene products useful as anthelmintics and fungicides are disclosed. The products may be prepared by several different methods including treating a 2-iminothioureidobenzene with a base and either an organic halide, a diester of sulfuric acid or a diester of sulfurous acid or treating a 2-aminoisothioureidobenzene with an appropriately substituted aldehyde.

50 Claims, No Drawings

2-IMINO SUBSTITUTED ISOTHIOUREIDOBENZENE

FIELD OF THE INVENTION

This invention relates to 2-imino substituted isothioureidobenzenes, to processes for making such compounds, to methods of treating helminth and fungus infections and to anthelmintic and antifungal compositions containing them.

DESCRIPTION OF THE INVENTION

British Pat. Nos. 1,214,415 and 1,307,250; U.S. Pat. Nos. 3,958,008; 3,860,586 and 3,836,569 and Netherlands Pat. No. 7,401,787 disclose numerous thioureas useful as anthelmintics, though none have a substituent on the sulfur. German Pat. No. 2,303,048 discloses 2-acylated amino-S-substituted isothioureidobenzenes are anthelmintics. However, there are no references disclosing compounds having both an imino substituent on the benzene ring and a substituted sulfur atom in the thioureido group. Other patents disclosing anthelmintic compounds include U.S. Pat. Nos. 3,865,948 and 4,005,217; also, British Pat. No. 1,350,277.

An object of this invention is to provide a new class of 2-imino substituted isothioureidobenzenes (I, infra), methods for preparing these compounds, compositions containing said compounds and to their use as anthelmintic and antifungal agents.

The novel 2-imino substituted isothioureidobenzenes (I, infra) of this invention have the following structural formula:

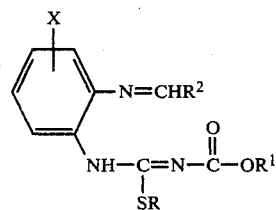

wherein R is alkyl, for example, lower alkyl of from 1 to 8 carbon atoms such as methyl, ethyl, n-propyl, n-butyl, iso-butyl, sec-butyl, pentyl, hexyl, heptyl, octyl and the like; alkenyl, for example, lower alkenyl of from 3 to 8 carbon atoms such as propenyl, butenyl, pentenyl, hexenyl, heptenyl, octenyl and the like; alkynyl, for example, lower alkynyl of from 3 to 8 carbon atoms such as propynyl, butynyl, pentynyl, hexynyl, heptynyl, octynyl and the like; polynuclear aralkyl such as napthylmethyl, napthylethyl, phenanthrenylmethyl and the like; mononuclear aralkyl such as benzyl, phenethyl, phenylpropyl and the like which may be ring-substituted with from 1 to 3 groups such as halo, alkyl, alkoxy, nitro, cyano and the like; mononuclear aryloxy lower alkyl, for example, phenoxy lower alkyl of from 3 to 6 carbon atoms in the alkyl group including phenoxypropyl, phenoxybutyl, phenoxypentyl, phenoxyhexyl and the like; cycloalkylalkyl, for example, cycloalkyl lower alkyl of from 5 to 6 nuclear carbon atoms such as cyclopentylmethyl, cyclopentylethyl, cyclohexylmethyl, cyclohexylethyl and the like; cyano lower alkyl of from 3 to 6 carbon atoms such as cyanopropyl, cyanobutyl, cyanopentyl, cyanohexyl and the like; hydroxy lower alkyl of from 3 to 8 carbon atoms such as hydroxypropyl, hydroxybutyl, hydroxypentyl, hydroxyoctyl and the like; aralkenyl, for example, poly- and mononuclear aralkenyl such as phenylpropenyl and the like; alkoxyalkyl, for example, lower alkoxy lower alkyl, such as methoxypropyl, ethoxypropyl, methoxybutyl, propoxybutyl and the like; alkoxycarbonylalkyl, for example, lower alkoxycarbonyl lower alkyl wherein lower alkyl has 3 to 6 carbon atoms, such as methoxycarbonylpropyl, ethoxycarbonylbutyl, ethoxycarbonylpentyl, propoxycarbonylhexyl and the like; phthalimido lower alkyl such as phthalimidobutyl and the like or phenoxycarbonylalkyl, for example, phenoxycarbonyl lower alkyl of from 3 to 6 carbon atoms such as phenoxycarbonyl propyl, phenoxycarbonyl butyl, phenoxycarbonylpentyl, phenoxycarbonylhexyl and the like; $R^1$ is alkyl, for example, lower alkyl of from 1 to 6 carbon atoms such as methyl, ethyl, n-propyl, isopropyl, n-butyl, iso-butyl, tert-butyl, pentyl, hexyl and the like or lower alkoxyalkyl such as methoxyethyl ethoxyethyl, propoxyethyl and the like; $R^2$ is alkyl, for example, lower alkyl of from 1 to 6 carbon atoms; substituted or unsubstituted aryl, of from 4 to 6 nuclear carbon atoms, for example, mononuclear aryl of from 4 to 6 nuclear carbon atoms, polynuclear aryl of from 10 to 14 carbon atoms, heteroaryl of from 5 to 6 nuclear atoms containing from 1 to 3 heteroatoms selected from oxygen, nitrogen or sulfur, examples of aryl include phenyl, naphthyl, thienyl, pyridyl, furyl, furylmethyl, pyrrolidinyl, pyrrolyl, isothiazolyl, oxadiazolyl, thiadiazolyl, imidazolyl, isooxazolyl, N-methylpyrryl, oxazolyl, pyrimidyl, and the like which may be unsubstituted or substituted with from 1 to 3 radicals selected from halo, such as chloro, bromo and the like, lower alkyl having from 1 to 5 carbon atoms, lower alkoxy having from 1 to 5 carbon atoms; di-lower alkylamino such as dimethylamino and the like, lower alkanoylamino of from 1 to 5 carbon atoms; phenoxy, benzyloxy, 3,4-lower alkylenedioxyphenyl, phenylthio lower alkyl, cyano, nitro, alkylthio or arylthio and the like; and X is hydrogen, nitro, halo, such as chloro, iodo, bromo fluoro and the like; lower alkanoyl of from 2 to 5 carbon atoms, such as acetyl, propionyl, butyryl, pentanoyl and the like; lower alkyl of from 1 to 4 carbon atoms such as methyl, ethyl, propyl, n-butyl and the like; lower alkoxy, such as methoxy, ethoxy, propoxy, butoxy, pentoxy and the like; thiocyanato, a radical of the formula: $Y-S(O)_n$ wherein Y is lower alkyl of from 1 to 5 carbon atoms; lower alkenyl ($C_3$-$C_6$), lower alkynyl ($C_3$-$C_6$), cyclo lower alkyl ($C_3$-$C_7$), a 5- or 6-membered heterocycle, such a pyridyl, thienyl, furyl, pyrimidyl, thiazolyl and the like or mononuclear aryl such as phenyl and n is an integer of 0 to 3, X is also lower alkylcarbonylamino, such as methylcarbonylamino and the like, lower ($C_1$-$C_4$) alkoxy carbonylamino such as methoxycarbonylamino, isopropoxycarbonylamino and the like, a 5- or 6-membered cycloalkylcarbonylamino such as cyclopentylcarbonylamino, cyclohexylcarbonylamino and the like; a radical of the formula:

wherein Y' is mononuclear aryl such as phenyl and the like; cyclo lower alkyl ($C_3$-$C_7$), a 5- or 6-membered heterocycle, such as pyridyl, 2-thienyl, furyl and the like or X is also a radical of the formula: Y"O— wherein Y" is lower alkyl ($C_1$-$C_5$), a mononuclear aryl, such as phenyl and the like, lower alkenyl, mononuclear arylkyl or a 5- or 6-membered heterocycle and, when substituted, the substituents on the Y, Y' and Y" are selected from halo, cyano, lower alkyl, lower alkoxy, lower alkanoyl, lower alkylthio, lower alkylsulfinyl, lower alkylsulfonyl, phenylthio, phenylsulfinyl, phenylsulfonyl, phenoxy, halophenoxy, benzyloxy, trifluoromethyl or carbo lower alkoxy and the nontoxic, pharmaceutically or agronomically acceptable acid addition salts such as those formed with acids such as hydrochloric, sulfuric, nitric, phosphoric, acetic, citric, benzoic, lactic and the like and amides of the ester such as amino, mono- and di-lower alkylamino and the like. Representative $R^2$ radicals include chlorophenyl, bromophenyl, methylphenyl, ethylphenyl, butylphenyl, pentylphenyl; 2,6-dichlorophenyl; 3,4-dichlorophenyl; methoxyphenyl, ethoxyphenyl, dimethylaminophenyl, acetamido; 3,4-methylenedioxyphenyl, methylthiophenyl, phenylthiophenyl and the like.

When compounds of general Formula I can exist in various isomer and stereoisomer forms, all such isomers and their mixtures and racemates are included within the scope of the present invention.

PREFERRED EMBODIMENT

A preferred embodiment of this invention relates to the 2-imino substituted isothioureidobenzenes (Ia, infra) of the following structural formula:

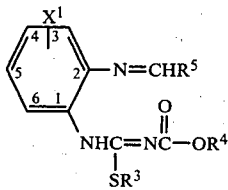

wherein $R^3$ is lower alkyl, lower alkenyl, lower alkynyl, benzyl, 2,6-dichlorobenzyl, phenethyl, cycloalkyl lower alkyl of from 5 to 6 nuclear atoms, phenoxy lower alkyl of from 3 to 6 carbon atoms, cyano lower alkyl of from 3 to 6 carbon atoms, lower alkoxy carbonyl lower alkyl wherein lower means from 3 to 6 carbon atoms, phthalimido lower alkyl, phenyl lower alkenyl of from 3 to 6 carbon atoms or hydroxy lower alkyl; $R^4$ is lower alkyl; $R^5$ is mononuclear aryl of from 4 to 6 nuclear carbon atoms, polynuclear aryl of from 10 to 14 nuclear carbon atoms or heteroaryl of from 5 to 6 nuclear atoms containing from 1 to 3 hetero atoms such as o, m, or p-nitrophenyl, o, m or p-dimethylaminophenyl, lower o, m or p-alkoxyphenyl, o, m or p-cyanophenyl, o, m or p-acetamidophenyl, methyenedioxyphenyl, phenyl, 2-furyl, 5-methyl-2-furyl, 2-thienyl, o, m, or p-halophenyl, lower o, m or p-alkyl phenyl or dihalophenyl and $X^1$ is in the 4 or 5 position of the benzene ring and is selected from hydrogen, lower alkyl carbonylamino, lower alkoxycarbonylamino, lower alkoxy, lower alkanoyl, propylthio, propylsulfinyl, propylsulfonyl, propylsulfonyloxy, propoxysulfonyl, phenylthio, phenylsulfinyl, phenylsulfonyl, phenoxysulfonyl, phenylsulfonyloxy or benzoyl. Especially preferred are those compounds wherein $X^1$ is hydrogen, 4-benzoyl, 5-propylthio or 5-phenylthio. These compounds exhibit particularly good anthelmintic and antifungal activity.

The products may be prepared by several alternative processes including treating a 2-imino substituted thioureidobenzene with a base and an organic halide, a diester of sulfuric acid or diester of sulfurous acid or by treating a 2-amino substituted isothioureidobenzene with an aldehyde.

The first method for preparing the 2-imino substituted isothioureidobenzene (I, supra) of this invention comprises treating the corresponding 2-imino substituted thioureidobenzene (II, infra) with a base, for example, an alkali metal or alkaline earth metal base, such as sodium hydride, calcium hydride, sodium hydroxide, potassium hydroxide, calcium hydroxide, potassium carbonate and the like followed by treatment with either an organic halide, a diester of sulfuric acid or diester of sulfurous acid. The reaction may be conducted at a temperature in the range of from $-10°$ C. to about 60° C. for a period of time of from a few minutes to about 24 hours. Any solvent in which the reactants are reasonable soluble and substantially inert may be employed. Suitable solvents include dimethylformamide, acetone, 1,2-dimethoxyethane, dimethyl sulfoxide and the like. The following equation illustrates this process:

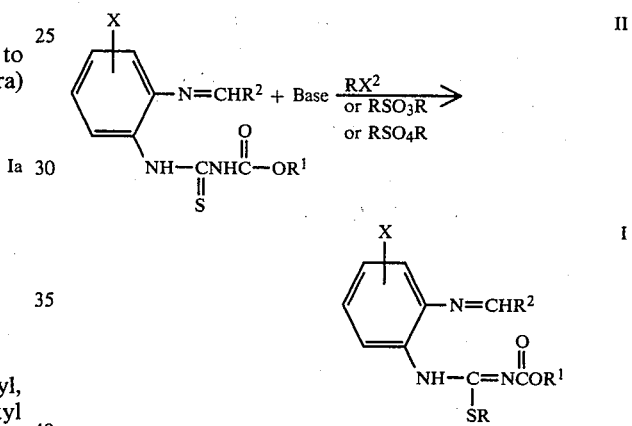

wherein R, $R^1$ and X are as defined above and $X^2$ is halo such as chloro, bromo or iodo.

A second method for preparing the compounds of Formula I comprises treating 2-amino substituted isothioureidobenzene with an aldehyde ($R^2CHO$) in a manner similar to that described below for the preparation of the compounds of Formula III. The following equation illustrates this process:

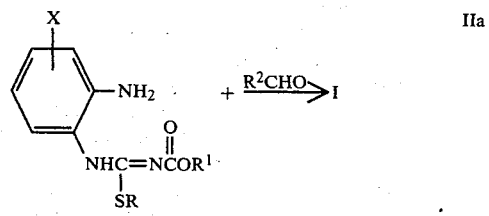

wherein R, $R^1$, $R^2$ and X are as defined above.

The compounds of Formula II are either known compounds or may be prepared by treating an appropriately substituted 1-imino-2-aminobenzene (III, infra) with a carboalkoxyisothiocyanate (IV, infra), to afford the desired compounds of Formula II. The following equation illustrates this process:

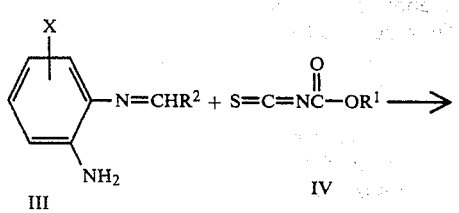

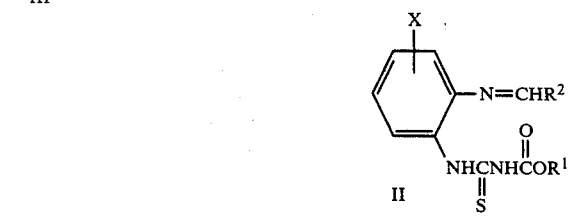

wherein $R^1$, $R^2$ and X are as defined above. This reaction is conveniently conducted in a suitable inert solvent such as diethyl ether, acetone, and the like for a period of time of from 30 minutes to 6 hours.

We have found that the compounds of Formula II, supra, which have been disclosed as anthelmintics are also useful as fungicides.

Compound IIa is prepared by the reaction of a thioureidobenzene (V, infra) where

with $RX^2$, $RSO_3R$ or $RSO_4R$ under the same conditions as described in the preparation of Formula I from Formula II.

The compounds of Formula II and also the compounds of Formula IIIa, 1-substituted-imino-2-substituted aminobenzene, may be prepared by treating the correspondingly substituted isothioureidobenzene or substituted 1,2-diaminobenzene (V, infra), respectively, with an aldehyde. The following equation illustrates this process:

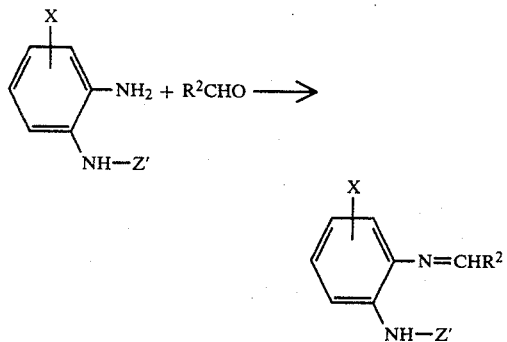

wherein $R^2$ and X are as defined above and Z' is hydrogen or

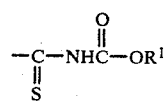

wherein $R^1$ is as defined above. This reaction is generally conducted at a temperature in the range of from about 0° C. to about 11° C. for a period of time of from one minute to about 24 hours. Suitable solvents which can be employed include acetone, methanol, ethanol, iso-propanol, methyl cellosolve, dimethylformamide, dimethyl sulfoxide and the like. An acid catalyst such as p-toluene sulfonic acid, sulfuric acid and the like may be employed. Any water formed during the reaction may be removed by azeotropic distillation.

When X is the radical YS, the sulfinyl (i.e., Y—SO—) and the sulfonyl product can be prepared by treating said YS substituted compound with one or two equivalents of an oxidizing agent, respectively. The oxidizing agent may be m-chloroperbenzoic acid, perbenzoic acid, peracetic acid, sodium hypochlorite and the like. The reaction is conducted at a temperature in the range of from −20° C. to 50° C. for a period of time of from about 5 minutes to 24 hours. Any substantially inert solvent in which the reactants are reasonably soluble may be employed including methylene dichloride, chloroform, carbon tetrachloride, benzene, toluene, chlorobenzene, acetone and the like.

The thioureidobenzene of Formula V

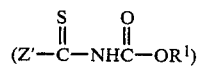

is prepared by treating a 1,2-diaminobenzene derivative or 1-amino-2-nitrobenzene derivative with a carboalkoxy isothiocyanate in the manner described above and when a nitrobenzene reducing said nitro to an amino group by reduction methods well-known to those skilled in the art.

2-Imino substituted isothioureidobenzenes of Formula I are anthelmintics and have broad spectrum activity against parasites of animals, especially warm blooded animals, including both mature and immature parasitic forms. In particular, these compounds exhibit high activity against various helmintic infections of the intestinal tract of economically important animals, coupled with low systemic toxicity to the host animal.

For example, the disclosed compounds are generally effective in clearing mice of worm infections, for laboratory purposes, including: *Syphacia obvelata* and *Aspicularis tetraptera*, the migratory stages of *Ascaris suum*, *Hymenolepsis nana* and *Nematospiroides dubius*.

Compounds of Formula I have been demonstrated as efficacious against gastrointestinal parasites in sheep, such as *Moniezia spp*, *Haemonchus contortus*, *Ostertagia spp*, *Trichostrongylus spp*, *Nematodirus spp*, *Trichuris ovis*, *Cooperia spp*, *Capillaria spp*, *Strongyloids papillosus*, *Bunostomum trigoncephalum* and *Oesophagostomum spp*. The compounds are active against lung worms in ruminants especially *Dictyocaulus filaria*, in sheep and *Dictyocaulus viviparus* and in cattle. The compounds (I) may also be used in treating *Fasciola gigantica* in cattle. In addition, the compounds are effective against liver flukes (*Fasciola hepatica*) in sheep and cattle.

Animals of low weight are treated with unit doses ranging no higher than a few milligrams; whereas, animals of high body weight, such as ruminants, require proportionately larger unit doses ranging up to several grams. Preferably, a single dose is administered for each animal species based on the weight of that species.

The amount of ingredient administered will depend on the weight of the host and will usually be a unit dosage between about 1 mg./kg. and 125 mg./kg. of body weight. It is contemplated that dosage units containing the compounds of Formula I of this invention as the essential active ingredient will be administered, orally or by injection, in the treatment and control of helmintic infections in man and domestic animals such as sheep, cattle, horses, dogs, cats, fish, swine and goats.

Further, applicants have found that the compounds of Formula I and Formula II of this invention display broad spectrum antifungal activity. It is contemplated, therefore, that antifungal compositions containing these compounds as an essential active ingredient will be employed in controlling the growth of fungi in or on animals and plants as well as in the paint, wood, textile, cosmetic, leather, tobacco, fur, rope, paper, pulp, plastic, fuel, rubber and food industries.

When used as an anthelmintic agent for the treatment and/or prevention of helminthiasis, the novel compounds of Formula I of this invention may be administered orally, rectally, intranasally, sublingually or topically, in a unit dosage form such as a capsule, bolus, tablet, suppository, paste, gel, spray, powder, ointment, cream or as a liquid drench. They may also be administered orally by intimately dispersing them in an animal feedstuff or by using them as a top dressing or in the form of pellets which are added to a finished feed. Alternatively, they may be administered to animals in a liquid carrier vehicle by intraruminal, interamuscular and intratracheal injection. In addition, polymeric implants providing a controlled release rate can be employed for administration. The quantity of active material required to give the best anthelmintic response will depend upon the particular compound employed, the species of animal to be treated and the type and severity of helminth infection. Good results are usually obtained when there is administered a total dose of from about 5 to about 125 mg. of active ingredient per kg. of animal body weight. Such total dose may be given at one time or in divided doses over a short period of time such as 1 to 3 days.

The 2-imino substituted isothioureidobenzenes and acid addition salts and metal salt complexes of the present invention are useful as agricultural fungicides and can be applied to various loci such as the seed, the soil or the foliage. The compounds can be employed in technical or pure form or in solutions or in formulations. The compounds are usually taken up in an agronomically acceptable carrier or are formulated to render them suitable for use as fungicides. For example, the compounds can be formulated as wettable powders, emulsifiable concentrates, dusts, granular formulations, aerosols, or flowable emulsion concentrates. In such formulations, the compounds are usually extended with an agronomically acceptable liquid or solid carrier and, when desired, suitable surfactants are also incorporated.

By the term "agronomically acceptable carrier" is meant any substance which can be utilized to dissolve, disperse, or diffuse the compounds without impairing the effectiveness of the compound and which is environmentally acceptable.

It is usually desirable, particularly in the case of foliar spray formulations, to include adjuvants, such as wetting agents, spreading agents, dispersing agents, stickers, adhesives and the like in accordance with the agricultural practices. Such adjuvants commonly used in the art can be found in the John W. McCutcheon, Inc. publication "Detergents and Emulsifiers, Annual."

In general, the compounds of this invention can be dissolved in organic solvents such as acetone, methanol, ethanol, dimethylformamide, pyridine, dimethyl sulfoxide and the like and the resulting solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, can be as high as about 75%.

Wettable powders suitable for spraying, can be prepared by admixing the compounds with a finely divided solid, such as clays, inorganic silicates and carbonates, and silicas and incorporating wetting agents, sticking agents, and/or dispersing agents. The concentration of active ingredients in these formulations is usually in the range of from about 20% to about 98%, preferably from about 40% to about 75%. A typical wettable powder is made by blending 50 parts of 1-imino(2-furylmethyl)-2-(3-carbomethoxy-S-butylisothioureido)benzene, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil wettable powder, and in another preparation 25% of the Hi-Sil is replaced with a synthetic sodium silico aluminate sold under the trademark Zeolex ® 7.

Dusts are prepared by mixing the compounds with finely divided inert organic or inorganic solids. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The compounds of this invention can be applied as fungicidal sprays by methods commonly employed, such as conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of fungicide coated on the seed is usually at a dosage rate of from about 0.1 to about 20 ounces per hundred pounds of seed. As a soil fungicide the compound can be incorporated in the soil or applied to the surface usually at a rate of from about 0.1 to about 50 lbs. per acre. As a foliar fungicide, the compound is usually applied to growing plants at a rate of from about 0.25 to about 10 lbs. per acre.

Fungicides which can be combined with the fungicides of this invention include:
 (a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl)phenyl crotonate (dinocap), 2-sec-butyl-4,6-dinitrophenyl-3,3-dimethylacrylate (binapacryl), and 2-sec-butyl-4,6-dinitrophenylisopropyl carbonate;

(c) Heterocyclic compounds such as N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole,5-amino-1-[bis-(dimethylamino)-phosphinyl]-3-phenyl-1,2,4-triazole, 5-ethoxy-3-trichloromethyl-1,2,4-triadiazole, 2,3-dicyano-1,4-dithiaanthraquinone (dithianon), 2-thio-1,3-dithio-[4,5-b] quinoxaline (thioquinox), methyl 1-(butylcarbamoyl)-2-benzimidazole carbamate (benomyl, 2-(4'-thiazolyl)benzimidazole (thiabendazole), 4-(2-chlorophenylhydrazone)-3-methyl-5-isoxazolone, pyridine-2-thio-1-oxide, 8-hydroxyquinoline sulfate and metal salts thereof; 2,3-dihydro-5-carboxanilido-6-methyl-1,4-oxathiin-4,4-dioxide-2,3-dihydro-5-carboxanili-do-6-methyl-1,4-oxathiin,α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethyl-amino-4-hydroxy-6-methylpyrimidine(ethirimol), acetate of 4-cyclododecyl-2,6-dimethylmorpholine (dodemorph), and 6-methyl-2-oxo-1,3-dithiolo-[4,5-b]quinoxaline (quinomethionate).

(d) miscellaneous halogenated fungicides such as tetrachloro-p-benzoquinone (chloranil), 2,3-dichloro-1,4-naphthoquinone (dichlone), 2,3-dichloro-2,5-dimethoxybenzene (chloroneb), 3,5,6-trichloro-o-anisic acid (tricamba), 2,4,5,6-tetrachloroisophthalo nitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethane-3,4,5,6,7,7-hexachlorophthalimide, phenylmercuric monoethanol ammonium lactate, p-dimethylaminobenzenediazo sodium sulfonate, methyl isothiacyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido) benzene (thiophenatemethyl).

The compounds of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the compounds of this invention will suggest themselves to those skilled in the art of agriculture and horticulture.

The following examples illustrate the compounds of this invention and the methods by which they may be prepared. However, the examples are illustrative only and it will be apparent to those having ordinary skill in the art that all of the products embraced by Formula I, supra, may also be prepared in an analogous manner by substituting the appropriate starting materials for those set forth in the examples.

EXAMPLE 1

3-Iminophenylmethyl-4-(3-carbomethoxy-S-methylisothioureido)benzophenone

Step A—3-Iminophenylmethyl-4-aminobenzophenone

To a solution of 3,4-diaminobenzophenone (4.24 g.; 0.02 mole) in methanol (50 ml.) cooled to 0° C. is added benzaldehyde (2.12 g.; 0.02 mole). The solution is stirred at 0° C. for one hour. The precipitate is collected by filtration and dried to yield 3.0 g. of 3-iminophenylmethyl-4-aminobenzophenone, m.p. 112°–116° C.

Elemental analysis for $C_{20}H_{16}N_2O$. Calc.: C, 79.97; H, 5.37; N, 9.33. Found: C, 80.11; H, 5.57; N, 9.28.

Step B—3-Iminophenylmethyl-4-(3-carbomethoxythioureido)benzophenone

To a solution of 3-iminophenylmethyl-4-aminobenzophenone (0.5 g.; 0.00166 mole) in diethylether (100 ml.) is added carbomethoxy isothiocyanate (0.19 g.; 0.00166 mole). The solution is stirred at room temperature for three hours. The precipitate is collected by filtration and dried to yield 0.35 g. of 3-iminophenylmethyl-4-(3-carbomethoxythioureido)benzophenone, m.p. 194°–195° C. (dec.).

Elemental analysis for $C_{23}H_{19}N_3O_3S$. Calc.: C, 66.17; H, 4.59; N, 10.07. Found: C, 65.81; H, 4.53; N, 9.80.

Step C—3-Iminophenylmethyl-4-(3-carbomethoxy-S-methylisothioureido)benzophenone

To a solution of 3-iminophenylmethyl-4-(3-carbomethoxythioureido)benzophenone (1.1 g.; 0.0026 mole) in dimethylformamide (10.0 ml.) is added water (3.0 ml.). Additional dimethylformamide (25.0 ml.) is added to dissolve some precipitate and then sodium hydroxide (50% aqueous; 0.21 g.; 0.0026 mole) is added. The resulting solution is stirred at room temperature for 1½ hours and then methyl iodide (0.38 g.; 0.0026 mole) is added. The solution is stirred for one hour at room temperature and then poured into water (250 ml.). The precipitate is collected by filtration and dried to afford 0.95 g. of 3-iminophenylmethyl-4-(3-carbomethoxy-S-methylisothioureido)benzophenone, m.p. 140°–142° C. (dec.).

Elemental analysis for $C_{24}H_{21}N_3O_3S$. Calc.: C, 66.80; H, 4.91; N, 9.74. Found: C, 65.68; H, 4.86; N, 10.44.

EXAMPLE 2

3-Iminophenylmethyl-4-(3-carbomethoxy-S-methylisothioureido)benzophenone

To a suspension of 3-iminophenylmethyl-4-(3-carbomethoxythioureido)benzophenone (2.09 g.; 0.005 mole) in a mixture of acetone (20 ml.) and water (3.0 ml.) is added aqueous sodium hydroxide solution (50%; 0.4 g.). The mixture is stirred for one hour at room temperature. To the solution is added methyl iodide (0.71 g.; 0.005 mole). Within two minutes a thick suspension forms. Additional acetone (20 ml.) and water (3.0 ml.) is added and stirring is continued for 18 hours.

The precipitate is collected by filtration and dried to afford 2.05 g. of 3-iminophenylmethyl-4-(3-carbomethoxy-S-methylisothioureido)benzophenone, m.p. 157°–158° C. (dec.).

Elemental analysis for $C_{24}H_{21}N_3O_3S$. Calc.: C, 66.80; H, 4.91; N, 9.74. Found: C, 66.31; H, 4.83; N, 9.95.

EXAMPLE 3

2-Imino(2,6-dichloro)phenylmethyl-4-(3-carbomethoxy-S-methylisothioureido)benzophenone Step A—2-Imino-(2,6-dichloro)phenylmethyl-4-aminobenzophenone To an ice cooled solution of 3,4-diaminobenzophenone (8.48 g.; 0.04 mole) in methanol (100 ml.) is added a solution of 2,6-dichlorobenzaldehyde (7.06 g.; 0.04 mole) in methanol (100 ml.). The solution is stirred at 0° C. for one hour and at room temperature over the weekend. The precipitate formed is collected by filtration and dried to afford 11.5 g. of 2-imino-(2,6-dichloro)-phenylmethyl-4-aminobenzophenone, m.p. 141°–144° C.

Step B—3-Imino(2,6-dichloro)phenylmethyl-4-(3-carbomethoxythioureido)benzophenone To a solution of 2-imino-(2,6-dichloro)-phenylmethyl-4-aminobenzophenone (2.08 g.; 0.005 mole) in diethyl ether (600 ml.) is added carbomethoxy isothiocyanate (0.88 g.; 0.0075 mole). The solution is stirred at room temperature for 18 hours. The precipitate which forms is collected and dried to yield 1.8 g. of 3-imino(2,6-dichloro)phenylmethyl-4-(3-carbomethoxythioureido)-benzophenone, m.p. 197° C. (dec.).

Elemental analysis for $C_{23}H_{17}Cl_2N_3O_3S$

Calc.: C, 56.79; H, 3.52; N, 8.64 Found: C, 57.49; H, 3.66; N, 8.84

Step C—3-Iminophenylmethyl-4-(3-carbomethoxy-S-methyl-isothioureido)benzophenone To a solution of 3-imino(2,6-dichloro)phenylmethyl-4-(3-carbomethoxythioureido)benzophenone (2.43 g.; 0.005 mole) in dimethylformamide (100 ml.) is added water (5.0 ml.) and then sodium hydroxide (50% aqueous; 0.4 g.; 0.005 mole). The solution is stirred for 1½ hours and then methyl iodide (0.71 g.; 0.005 mole) is added. The solution is stirred for one-half hour. The precipitate which forms is collected by filtration and dried to afford 1.3 g. of 3-iminophenylmethyl-4-(3-carbomethoxy-S-methylisothioureido)benzophenone, m.p. 63°–68° C. (dec.).

Elemental analysis for $C_{24}H_{19}Cl_2N_3O_3S$. Calc.: C, 57.60; H, 3.83; N, 8.40; S, 6.41. Found: C, 56.65; H, 3.80 N, 8.48; S, 5.84.

EXAMPLE 4

3-Imino-(4-methylphenyl)methyl-4-(3-carbomethoxy-S-methylisothioureido)benzophenone Step A—3-Imino-(4-methylphenyl)methyl-4-aminobenzophenone To an ice cooled solution of 3,4-diaminobenzophenone (6.36; 0.03 mole) in methanol (75 ml.) is added p-tolualdehyde (3.6 g.; 0.03 mole). The solution is stirred at 5° C. for one hour and at room temperature for 18 hours. A precipitate is collected by filtration and dried to afford 4.5 g. of 3-imino-(4-methyl)phenylmethyl-4-aminobenzophenone, m.p. 136°–137° C.

Step B—3-Imino-(4-methylphenyl)methyl-4-(3-carbomethoxythioureido)benzophenone

To a solution of 3-imino-(4-methylphenyl)methyl-4-aminobenzophenone (4.5 g.; 0.0145 mole) in dimethoxyethane (75 ml.) and diethyl ether (25 ml.) is added carbomethoxy isothiocyanate (1.68 g.; 0.0145 mole). The solution is stirred at room temperature for 10 minutes at which time a precipitate begins to form. Stirring is continued at room temperature for one hour and the precipitate is collected by filtration and dried to afford 3.9 g. of 3-imino-(4-methylphenyl)methyl-4-(3-carbomethoxythioureido)benzophenone, m.p. 201°–202° C. (dec.).

Elemental analysis for $C_{24}H_{21}N_3O_3S$. Calc.: C, 66.80; H, 4.91; N, 9.74. Found: C, 66.73; H, 4.79; N, 10.18.

Step C—3-Imino-(4-methylphenyl)methyl-4-(3-carbomethoxy-S-methylisothioureido)benzophenone To a solution of 3-imino-(4-methylphenyl)methyl-4-(3-carbomethoxythioureido)benzophenone (2.0 g.; 0.00463 mole) in dimethylformamide (100 ml.) and water (5 ml.) is added sodium hydroxide (50% aqueous; 0.37 g.). The solution is stirred at room temperature for one hour at which time methyl iodide (0.66 g.; 0.00463 mole) is added. The solution is stirred at room temperature for 20 minutes and then poured into water (1.0 l.). A precipitate forms and is collected by filtration and dried to afford 2.1 g. of 3-imino-(4-methylphenyl)methyl-4 (3-carbomethoxy-S-methylisothioureido)benzophenone, m.p. 40°–45° C. (dec.).

Elemental analysis for $C_{25}H_{23}N_3O_3S$. Calc.: C, 67.39; H, 5.20; N, 9.43; S, 7.20. Found: C, 66.81; H, 5.22; N, 9.94; S, 7.23.

EXAMPLE 5

3-Imino-(4-chlorophenyl)methyl-4-(3-carbomethoxy-S-methylisothioureido)benzophenone Step A—3-Imino (4-chlorophenyl)methyl-4-aminobenzophenone To an ice cooled solution of 3,4-diaminobenzophenone (8.4 g.; 0.04 mole) in methanol (100 ml.) is added p-chlorobenzaldehyde (5.6 g.; 0.04 mole). The solution is stirred at 0°–5° C. for one hour and at room temperature for 18 hours. The precipitate which formis is collected and dried to afford 9.2 g. of 3-imino(4-chlorophenyl)methyl-4-aminobenzophenone, m.p. 123°–125° C.

Elemental analysis for $C_{20}H_{15}ClNO_2O$. Calc.: C, 71.74; H, 4.52; H, 8.37. Found: C, 71.87; H, 4.43; N, 8.60.

Step B—3-Imino-(4-chlorophenyl)methyl-4-(3-carbomethoxythioureido)benzophenone

To a solution of 3-imino-(4-chloro)-phenylmethyl-4 aminobenzophenone (7.9 g.; 0.02 mole) in diethyl ether (700 ml.) is added carbomethoxy isothiocyanate (2.34 g.; 0.02 mole). The solution is stirred at room temperature for 18 hours. The precipitate which forms is collected by filtration and dried to afford 6.6 g. of 3-imino-(4-chloro)phenylmethyl-4-(3 carbomethoxythioureido)-benzophenone, m.p. 212°–216° C. (dec.).

Elemental analysis for $C_{23}H_{18}ClN_3O_3S$. Calc.: C, 61.12; H, 4.01; N, 9.30. Found: C, 61.37; H, 4.06; N, 9.72.

Step C—3-Imino-(4-chlorophenyl)methyl-4-(3-carbomethoxy-S-methylisothioureido)benzophenone To a solution of 3-imino-(4-chlorophenyl)methyl-4-(3-carbomethoxythioureido)benzophenone (4.52 g; 0.01 mole) in dimethylformamide (200 ml.) and water (5.0 ml.) is added aqueous sodium hydroxide (50% aqueous; 0.8 g.). The solution is stirred at room temperature for one hour and then methyl iodide (1.42 g.; 0.01 mole) is added. The solution is stirred at room temperature for 25 minutes and then poured into water (700 ml.). The suspension which forms is then stirred for 5 minutes and the precipitate is collected by filtration and dried to afford 4.3 g. of 3-imino-(4-chlorophenyl)methyl-4-(3-carbomethoxy-S-methylisothioureido)benzophenone, m.p. 156°–157° C. (dec.).

Elemental analysis for $C_{24}H_{20}ClN_3O_3S$. Calc.: C, 61.86; H, 4.33; N, 9.02. Found: C, 60.97; H, 4.21; N, 9.02. Found: C, 60.97; H, 4.21; N, 9.51.

EXAMPLE 6

3-Iminophenylmethyl-4-(3-carbomethoxy-S-benzylisothioureido)benzophenone

To a solution of 3-iminophenylmethyl-4-(3-carbomethoxythioureido)benzophenone (2.35 g.; 0.0054 mole) in dimethylformamide (100 ml.) and water (10 ml.) there is added aqueous sodium hydroxide solution (50%; 0.44 g.). The solution is stirred at room temperature for one hour and then benzyl bromide (0.93 g.; 0.0054 mole) is added. The solution is stirred at room temperature for 15 minutes and is then poured into 500 ml. of water. The suspension which forms is stirred at room temperature for 5 minutes and then collected by filtration and dried to afford 2.45 g. of 3-iminophenylmethyl-4-(3-carbomethoxy-S-benzylisothioureido)benzophenone, m.p. 50°–70° C. (dec.).

Elemental analysis for $C_{30}H_{25}N_3O_3S$. Calc.: C, 70.98; H, 4.96; N, 8.28. Found: C, 69.44; H, 4.98; N, 8.90.

EXAMPLE 7

3-Iminophenylmethyl-4-(3-carbomethoxy-S-allylisothioureido)benzophenone

To a suspension of 3-iminophenylmethyl-4-(3-carbomethoxythioureido)benzophenone (2.09 g.; 0.005 mole) in acetone (40 ml.) and water (6.0 ml.) is added an aqueous sodium hydroxide solution (50% aqueous; 0.4 g.). The suspension is stirred at room temperature for one hour and then allyl bromide (0.6 g.; 0.005 mole) is added and the solution is stirred at room temperature over the weekend. The precipitate which forms is collected by filtration and then dried to afford 1.3 g. of 3-iminophenylmethyl)-4-(3-carbomethoxy-S-allylisothioureido)benzophenone, m.p. 125°–127° C.

Elemental analysis for $C_{26}H_{23}N_3O_3S$. Calc.: C, 68.25; H, 5.07; N, 9.18. Found: C, 67.93; H, 4.98; N, 8.79.

EXAMPLE 8

1-(3-Carbomethoxy-S-methylisothioureido)-2-iminophenylmethyl-5-propylthiobenzene Step A—1-(3-Carbomethoxythioureido)-2-nitro-5-propylthiobenzene To a stirred mixture of 2-nitro-5-propanylthioaniline (21.2 g.; 0.10 mole) in acetonitrile (50 ml.) is added portionwise carbomethoxy isothiocyanate (11.7 g.; 0.10 mole). The reaction mixture is maintained at room temperature and is filtered to remove a small amount of dark colored insoluble material. The clear filtrate was permitted to stand at room temperature for two hours and the precipitate which forms is collected by filtration, washed with cold acetonitrile and dried to yield 1-(3-carbomethoxythioureido)-2-nitro-5-propylthiobenzene (17.6 g.), m.p. 122°–125° C.

Step B—1-(3-Carbomethoxythioureido)-2-amino-5-propylthiobenzene

A mixture of 1-(3-carbomethoxythioureido)-2-nitro-5-propylthiobenzene (4.4 g.; 0.0134 mole), stannous chloride (15.2 g.; 0.067 mole), concentrated hydrochloric acid (25 ml.), methanol (50 ml.) and acetic acid (50 ml.) is stirred and refluxed for one half hour. The reaction mixture is poured into ice water and basified with 50% aqueous sodium hydroxide solution. This solution is extracted with dichloromethane and the dichloromethane removed to afford 3.8 g. of 1-(3 carbomethoxythioureido)-2-amino-5-propylthiobenzene.

Step C—1-(3-Carbomethoxythioureido)-2-iminophenylmethyl-5-propylthiobenzene

To an ice-cooled solution of 1-(3-carbomethoxythioureido)-2 amino-5-propylthiobenzene (1.0 g.; 0.00334 mole) in methanol (100 ml.) is added benzaldehyde (0.35 g.; 0.00334 mole). The solution is stirred at 5° C. for an hour and the precipitate which forms is collected by filtration and dried to afford 0.6 g. of 1-(3-carbomethoxythioureido)-2-iminophenylmethyl-5-propylthiobenzene, m.p. 109°–110° C.

Elemental analysis for $C_{19}H_{21}N_3O_2S_2$. Calc.: C, 58.89; H, 5.46; N, 10.84. Found: C, 58.85; H, 5.46; N, 11.02.

Step D—1-(3-Carbomethoxy-S-methylisothioureido)-2-iminophenylmethyl-5-propylthiobenzene To a solution of 1-(3-carbomethoxythioureido)-2-iminophenylmethyl-5-propylthiobenzene (0.5 g.; 0.00129 mole) in acetone (20 ml.) and water (3.0 ml.) is added an aqueous sodium hydroxide solution (50%; 0.103 g.). The solution is stirred at room temperature for 1½ hours and then methyl iodide (0.183 g.; 0.00129 mole) is added. The reaction mixture is stirred at room temperature for one hour and then poured in water (100 ml.). The suspension formed is stirred at room temperature for 1½ hours and then the precipitate collected by filtration and dried to afford 0.35 g. of 1-(3 carbomethoxy-S-methylisothioureido) 2-iminophenylmethyl-5-propylthiobenzene, m.p. 80°–83° C. (dec.).

Elemental analysis for $C_{20}H_{23}N_3O_3S_2$. Calc.: C, 59.82; H, 5.77; N, 10.46; S, 15.97. Found: C, 59.73; H, 5.88; N, 10.36; S, 15.89.

EXAMPLE 9

1-(3-Carbomethoxy-S-methylisothioureido)-2-iminophenylmethyl-4-benzenesulfonylbenzene Step A—2-Iminophenylmethyl-4-benzenesulfonylaniline To an ice-cooled solution of 2-amino-4-benzenesulfonylaniline (5.2 g.; 0.021 mole) in methanol (25 ml.) is added benzaldehyde (2.23 g.; 0.021 mole). The solution is stirred at 0° C. for 1½ hours. A suspension forms which is stirred at room temperature overnight and then the precipitate collected by filtration is washed with methanol and then ether and then dried to afford 6.0 g. of 2-iminophenylmethyl-4-benzenesulfonylaniline, m.p. 159°–160° C.

Elemental analysis for $C_{19}H_{16}N_2O_2S$. Calc.: C, 67.83; H, 4.79; N, 8.33. Found: C, 67.54; H, 4.90; N, 8.62.

Step B—1-(3-Carbomethoxythioureido)-2-iminophenylmethyl-4-benzenesulfonylbenzene To a solution of 2-iminophenylmethyl-4-benzenesulfonylaniline (4.5 g.; 0.0134 mole) in acetone (250 ml.) is added carbomethoxy isothiocyanate (1.57 g.; 0.0134 mole). The solution is stirred at room temperature for two hours and the precipitate which forms is collected by filtration, washed with ether and dried to afford 2.15 g. of 1-(3-carbomethoxythioureido)-2-iminophenylmethyl-4-benzenesulfonylbenzene, m.p. 207°–208° C. (dec.).

Elemental analysis for $C_{22}H_{19}N_3O_4S_2$. Calc.: C, 58.26; H, 4.22; N, 9.27. Found: C, 58.32; H, 4.14; N, 9.40.

Step C—1-(3-Carbomethoxy-S-methylisothioureido)-2-iminophenylmethyl-4-benzenesulfonylbenzene To a suspension of 1-(3-carbomethoxythioureido)-2-iminophenylmethyl-4-benzenesulfonylbenzene (1.0 g.; 0.0022 mole) in acetone (10 ml.) and water (1.0 ml.) there is added an aqueous sodium hydroxide solution (50%; 0.18 g.). This mixture is stirred at room temperature for 2 hours and a fine suspension which forms is removed by filtration. To the filtrate is added methyl iodide (0.313 g.; 0.0022 mole). The solution is stirred at room temperature for 8 days. The reaction mixture is filtered and to the filtrate is added water (300 ml.) and the resulting mixture is stirred at room temperature for 3 hours. The precipitate which forms is collected by filtration and dried to afford 0.3 g. of 1-(3-carbomethoxy-S-methylisothioureido)-2-iminophenylmethyl-4-benzenesulfonylbenzene.

Elemental analysis for $C_{23}H_{21}N_3O_4S_2$. Calc.: C, 59.08; H, 4.53; N, 8.99. Found: C, 58.67; H, 4.39; N, 8.79.

EXAMPLE 10

3-Iminophenylmethyl-4-(3-carbomethoxy-S-butylisothioureido)benzophenone

To a suspension of 3-iminophenylmethyl-4-(3-carbomethoxythioureido)benzophenone (3.12 g.; 0.0075 mole) in acetone (60 ml.) and water (10 ml.) there is added an aqueous solution of sodium hydroxide (50%; 0.6 g.). The mixture is stirred at room temperature for 1¼ hours and to the solution form there is added n-butyl iodide (1.38 g.; 0.0075 mole). The solution is stirred at room temperature for 2 hours and the suspension which forms is collected by filtration, washed with ether and dried to afford 1.9 g. of 3-iminophenylmethyl-4-(3-carbomethoxy-S-n-butylisothioureido)benzophenone, m.p. 105°–107° C. (dec.).

Elemental analysis for $C_{27}H_{27}N_3O_3S$. Calc.: C, 68.47; H, 5.75; N, 8.87. Found: C, 67.56; H, 5.77; N, 8.52.

EXAMPLE 11

3-Iminophenylmethyl-4-[3-carbomethoxy-S-(2,6-dichlorophenyl)isothioureido]benzophenone To a suspension of 3-iminophenylmethyl-4-(3-carbomethoxythioureido)benzophenone (3.12 g.; 0.0075 mole) in acetone (60 ml.) and water (10 ml.) is added an aqueous solution of sodium hydroxide (50%; 0.6 g.). The mixture is stirred at room temperature for 2 hours and then α-bromo-2,6-dichlorotoluene (1.3 g.; 0.0075 mole) is added. This solution is stirred at room temperature for one half hour. The precipitate which forms is collected by filtration, washed with ether and dried to afford 2.5 g. of 3-iminophenylmethyl-4-[3-carbomethoxy-S-(2,6-dichlorophenyl)isothioureido]benzophenone, m.p. 148°–150° C. (dec.).

Elemental analysis for $C_{30}H_{23}Cl_2N_3O_3S$. Calc.: C, 62.50; H, 4.02; N, 7.29. Found: C, 61.64; H, 3.95; N, 7.21.

EXAMPLE 12

3-(Imino-(4-nitrophenyl)methyl-4-(3-carbomethoxy-S-methylisothioureido)benzophenone Step A—3-Imino-(4-nitrophenyl)methyl-4-aminobenzophenone To a solution of 3,4-diaminobenzophenone (8.48 g.; 0.04 mole) in methanol (100 ml.) is added p-nitrobenzaldehyde (6.04 g.; 0.04 mole). The reaction mixture is stirred for 5 days and the precipitate is collected by filtration and dried to afford 12.45 g. of 3-imino-(4-nitrophenyl)methyl-4-aminobenzophenone, m.p. 161°–163° C. (dec.).

Step B—3-Imino-(4-nitrophenylmethyl)-4-(3-carbomethoxythioureido)benzophenone

To a solution of 3-imino-(4-nitrophenylmethyl-4 aminobenzophenone (6.9 g.; 0.02 mole) in acetone (225 ml.) there is added carbomethoxy isothiocyanate (2.34 g.; 0.02 mole). The solution is stirred at room temperature for 18 hours. The precipitate which forms is collected by filtration and then dried to afford 7.35 g. of 3-imino-(4 nitrophenylmethyl)-4-(3-carbomethoxythioureido)-benzophenone, m.p. 229°–230° C. (dec.).

Step C—3-Imino-(4-nitrophenyl)methyl-4-(3-carbomethoxy-S-methylisothioureido)benzophenone To a suspension of 3 imino-(4-nitrophenylmethyl)-4 (3 carbomethoxythioureido)benzophenone (4.62 g.; 0.01 mole) in acetone (160 ml.) and water (24 ml.) there is added an aqueous solution of sodium hydroxide (50%; 0.8 g.). The solution is stirred at room temperature for one hour at which time methyl iodide (1.42 g.; 0.01 mole) is added. The suspension forms and the reaction mixture is stirred for 30 minutes. The precipitate is collected by filtration, washed with ether and dried to afford 2.55 g. of 3-imino-(4-nitrophenyl)methyl-4-(3-carbomethoxy-S-methylisothioureido)benzophenone, m.p. 180°–182° C. (dec.).

Elemental analysis for $C_{24}H_{20}N_4O_5S$. Calc.: C, 60.49; H, 4.23; N, 11.76. Found: C, 60.90; H, 4.33; N, 11.87.

EXAMPLE 13

3-Imino-(2-napthylmethyl)-4 (3-carbomethoxy-S-methylisothioureido)benzophenone

Step A—3-Imino-(2-napthylmethyl)-4-aminobenzophenone

To an ice cooled solution of 3,4-diaminobenzophenone (10.6 g.; 0.05 mole) in methanol (120 ml.) is added 2-napthaldehyde (7.8 g.; 0.05 mole). The solution is stirred at 5° C. for 2 hours at room temperature overnight. Sulfuric acid (5 drops) is added and the solution stirred an additional 5 days at room temperature. The precipitate is collected by filtration and dried to afford 5.25 g. of 3-imino-(4-nitrophenyl)methyl-4-aminobenzophenone, m.p. 141°–143° C. (dec.).

Elemental analysis for $C_{24}H_{18}N_2O$. Calc.: C, 82.26; H, 5.18; N, 8.00. Found: C, 81.53; H, 4.98; N, 7.19.

Step B—3-Imino-(2-napthylmethyl)-4-(3-carbomethoxythioureido)benzophenone

To a solution of 3-imino-(2-napthyl)-4-(aminobenzophenone) (4.0 g.; 0.0114 mole) in acetone (50 ml.) is added carbomethoxy isothiocyanate (1.34 g.; 0.0114 mole). A suspension forms within 5 minutes and stirring is continued at room temperature for 18 hours. The precipitate is collected by filtration, washed successively with acetone and ether and then dried to afford 3.1 g. of 3-imino-(2-napthylmethyl)-4-(3-carbomethoxy-thioureido)-benzophenone, m.p. 207°–209° C. (dec.).

Elemental analysis for $C_{27}H_{21}M_3O_3S$. Calc.: C, 69.36; H, 4.53; N, 8.99. Found: C, 69.37; H, 4.58; N, 8.83.

Step C—3-Imino-(2-napthylmethyl)-4-(3-carbomethoxy-S-methylisothioureido)-benzophenone To a suspension of 3-imino-(2-napthylmethyl)-4-(3-carbomethoxythioureido)benzophenone (2.5 g.; 0.0535 mole) in acetone (25 ml.) and water (3 ml.) there is added an aqueous sodium hydroxide solution (50%; 0.43 g.). The mixture is stirred at room temperature for 18 hours and then filtered. To the filtrate is added methyl iodide (0.76 g.; 0.00535 mole). The precipitate forms within 5 minutes. The suspension is stirred at room temperature for 30 minutes and the precipitate is collected by filtration, washed with ether and dried to afford 0.8 g. of 3-imino-(2-napthylmethyl)-4-(3-carbomethoxy-S-methylisothioureido)benzophenone, m.p. 147°–149.5° C. (dec.).

Elemental analysis for $C_{28}H_{23}N_3O_3S$. Calc.: C, 69.83; H, 4.81; N, 8.73. Found: C, 69.28; H, 4.82; N, 8.50.

EXAMPLE 14

3-Imino-(4-methoxyphenylmethyl) 4-(3 carbomethoxy-S-methylisothioureido)benzophenone Step A—3-Imino-(4-methoxyphenylmethyl)-4-aminobenzophenone To an ice-cooled solution of 3,4-diaminobenzophenone (10.6 g.; 0.05 mole) in methanol (120 ml.) is added p-anisaldehyde (6.8 g.; 0.05 mole). The solution is stirred at 5° C. for 2 hours and at room temperature for 18 hours. Sulfuric acid (5 drops) is added to the solution and it is stirred an additional 9 days at room temperature. The precipitate is collected by filtration, washed with ether and then dried to afford 4.2 g. of 3-amino-(4-methoxyphenylmethyl)-4-aminobenzophenone, m.p. 129°–131° C. (dec.).

Step B—3-Imino-(4-methoxyphenylmethyl)-4-(3-carbomethoxythioureido)benzophenone

To a solution of 3-imino-(4-methoxyphenylmethyl)-4-aminobenzophenone (4.29 g.; 0.0127 mole) in acetone (75 ml.) is added carbomethoxy isothiocyanate (1.49 g.; 0.027 mole). The solution is stirred at room temperature for 18 hours (a precipitate forms within 3 minutes). The precipitate is collected by filtration, washed with ether and then dried to afford 3.3 g. of 3-imino-(4-methoxyphenylmethyl)-4-(3-carbomethoxythioureido)benzophenone, m.p. 182°–184° C. (dec.).

Step C—3-Imino-(4-methoxyphenylmethyl) 4-(3-carbomethoxy-S-methylisothioureido)benzophenone To a suspension of 3-imino-(4-methoxyphenylmethyl)-4-(3-carbomethoxythioureido)benzophenone (2.5 g.; 0.0056 mole) in acetone (20 ml.) and water (4 ml.) there is added an aqueous solution of sodium hydroxide (50%; 0.45 g.). The reaction mixture is stirred at room temperature for two hours. A solid which forms is removed by filtration and to the clear filtrate is added methyl iodide (0.79 g.; 0.0056 mole). A precipitate forms within 5 minutes. The suspension is stirred at room temperature for 30 minutes and the precipitate is collected by filtration, washed with ether and dried to afford 1.1 g. of 3-imino-(4-methoxyphenylmethyl)-4-(3-carbomethoxy-S-methylisothioureido)benzophenone, m.p. 136°–138° C. (dec.).

Elemental analysis for $C_{25}H_{23}N_3O_4S$. Calc.: C, 65.06; H, 5.02; N, 9.10. Found: C, 64.87. H, 5.04; N, 8.87.

EXAMPLE 15

3-Imino-(2-nitrophenylmethyl)-4-(3-carbomethoxy-S-methylisothioureido)benzophenone Step A—3-Imino-(2-nitrophenylmethyl)-4-aminobenzophenone To an ice-cooled solution of 3,4-diaminobenzophenone (8.48 g.; 0.04 mole) in methanol (100 ml.) there is added o-nitrobenzaldehyde (6.04 g.; 0.04 mole). The mixture is stirred at 5° C. for one hour and at room temperature for 18 hours. Sulfuric acid (3 drops) is added to the solution and then within one hour a suspension forms. The suspension is stirred at room temperature for 18 hours and a precipitate collected by filtration, washed with ether and dried to afford 10.85 g. of 3-imino-(2 nitrophenylmethyl)-4 aminobenzophenone, m.p. 140°–142° C. (dec.). This material is used in the next step without further purification.

Step B—3-Imino-(2-nitrophenylmethyl)-4-(3-carbomethoxythioureido)benzophenone

To a solution of 3 imino-(2-nitrophenylmethyl)-4-aminobenzophenone (10.0 g.; 0.029 mole) in acetone (100 ml.) is added carbomethoxy isothiocyanate (3.4 g.; 0.029 mole). The solution is stirred at room temperature for 3 hours and the precipitate collected by filtration and dried to afford 7.3 g. of 3-imino-(2-nitrophenylmethyl)-4-(3-carbomethoxythioureido)benzophenone, m.p. 215°–217° C. (dec.).

Elemental analysis for $C_{23}H_{18}N_4O_5S$. Calc.: C, 59.73; H, 3.92; N, 12.12. Found: C, 59.65; H, 3.98; N, 12.28.

Step C—3-Imino-(2-nitrophenylmethyl)-4-(3-carbomethoxy-S-methylisothioureido)-benzophenone To a suspension of 3-imino-(2-nitrophenylmethyl)-4-(3-carbomethoxythioureido)benzophenone (4.62 g.; 0.01 mole) in acetone (160 ml.) and water (24 ml.) is added an aqueous solution of sodium hydroxide (50%; 0.8 g.). The mixture is stirred at room temperature for one hour and a fine precipitate which forms is removed by filtration. To the filtrate is added methyl iodide (1.42 g.; 0.01 mole) and the solution stirred at room temperature for 45 minutes. The precipitate which forms is collected by filtration and dried to afford 2.65 g. of 3-imino-(2-nitrophenylmethyl)-4-(3-carbomethoxy-S-methylisothioureido)benzophenone, m.p. 167°–168.5° C. (dec.).

Elemental analysis for $C_{24}H_{20}N_4O_5S$. Calc.: C, 60.49; H, 4.23; N, 11.76. Found: C, 60.56; H, 4.26; N, 11.65.

EXAMPLE 16

3-Imino-(3,4-dichlorophenylmethyl)-4-(3-carbomethoxy-S-methylisothioureido)benzophenone Step A—3-Imino-(3,4-dichlorophenylmethyl)-4-aminobenzophenone To a solution of 3,4-diaminobenzophenone (6.15 g.; 0.029 mole) in methanol (100 ml.), cooled to 5° C., is added 3,4-dichlorobenzaldehyde (5.08 g.; 0.029 mole). The mixture is stirred at 5° C. for one hour and at room temperature for 18 hours. The precipitate which forms is collected by filtration and dried to afford 7.96 g. of 3-imino-(3,4-dichlorophenylmethyl)-4-aminobenzophenone, m.p. 147°–148° C.

Elemental analysis for $C_{20}H_{14}Cl_2N_2O$. Calc.: C, 65.05; H, 3.82; N, 7.59. Found: C, 64.60; H, 3.79; N, 7.49.

Step B—3-Imino-(3,4-dichlorophenylmethyl)-4-(3-carbomethoxythioureido)benzophenone To a solution of 3-imino-(3,4-dichlorophenylmethyl)-4-aminobenzophenone (7.0 g.; 0.019 mole) in acetone (200 ml.) there is added carbomethoxy isothiocyanate (2.22 g.; 0.019 mole). A precipitate forms within five minutes. The mixture is stirred at room temperature for 1½ hours and the precipitate which forms is collected by filtration, washed with acetone and then ether and then dried to afford 6.9 g. of 3-imino-(3,4-dichlorophenylmethyl)-4-(3-carbomethoxythioureido)benzophenone, m.p. 214°–216° C. (dec.).

Elemental analysis for $C_{23}H_{17}Cl_2N_3O_3S$. Calc.: C, 56.79; H, 3.52; N, 8.64. Found: C, 56.76; H, 3.53; N, 8.43.

Step C—3-Imino-(3,4-dichlorophenylmethyl)-4-(3-carbomethoxy-S-methylisothioureido)benzophenone To a solution of 3-imino-(3,4-dichlorophenylmethyl)-4-(3-carbomethoxythioureido)benzophenone (3.0 g.; 0.0062 mole) in dimethylformamide (225 ml.) and water (10 ml.) there is added an aqueous sodium hydroxide solution (50%; 0.49 g.). The solution is stirred at room temperature for one hour and then methyl iodide (0.88 g.; 0.0062 mole) is added. The solution is stirred at room temperature for 20 minutes and then poured into water (1.0 l.). The suspension is filtered to collect the precipitate and then dried to afford 2.55 g. of 3-imino-(3,4-dichlorophenylmethyl)-4-(3-carbomethoxy-S-methylisothioureido)benzophenone, m.p. 168°–174° C. (dec.).

Elemental analysis for $C_{24}H_{19}Cl_2N_3O_3S$. Calc.: C, 57.60; H, 3.83; N, 8.40. Found: C, 57.22; H, 3.79; N, 8.24.

EXAMPLE 17

3-Imino-(2-chlorophenylmethyl)-4-(3-carbomethoxy-S-methylisothioureido)benzophenone Step A—3-Imino-(2-chlorophenylmethyl)-4-aminobenzophenone To an ice-cooled solution of 3,4-diaminobenzophenone (16.96 g.; 0.08 mole) in methanol (200 ml.) is added o-chlorobenzaldehyde (11.2 g.; 0.08 mole). The solution is stirred at room temperature for 30 minutes and the precipitate which separates is collected by filtration and dried to afford 20.5 g. of 3-imino-(2-chlorophenylmethyl)-4-aminobenzophenone, m.p. 112° C. (dec.).

Step B—3-Imino-(2-chlorophenylmethyl)-4-(3-carbomethoxythioureido)benzophenone

To a solution of 3-imino-(2-chlorophenylmethyl)-4-aminobenzophenone (11.85 g.; 0.03 mole) in acetone (100 ml.) is added carbomethoxy isothiocyanate (3.51 g.; 0.03 mole). It is necessary to add another portion of acetone (100 ml.) to the thick suspension which forms. The reaction mixture is stirred for an additional 30 minutes and the precipitate collected by filtration and dried to afford 9.0 g. of 3-imino-(2-chlorophenylmethyl)-4-(3-carbomethoxythioureido)benzophenone, m.p. 204°–205° C. (dec.).

Elemental analysis for $C_{23}H_{18}ClN_3O_3S$. Calc.: C, 61.12; H, 4.01; N, 9.30. Found: C, 60.93; H, 4.00; N, 9.19.

Step C—3-Imino-(2-chlorophenylmethyl)-4-(3-carbomethoxy-S-methylisothioureido)benzophenone To a suspension of 3-imino-(2-chlorophenylmethyl)-4-(3-carbomethoxythioureido)benzophenone (3.0 g.; 0.0066 mole) in acetone (50 ml.) and water (10 ml.) is added an aqueous solution of sodium hydroxide (50%; 0.53 g.). The mixture is stirred at room temperature for one hour and then methyl iodide (0.94 g.; 0.0066 mole) is added. The solution is stirred at room temperature over the week-end and the precipitate which forms is collected by filtration and dried to afford 0.9 g. of 3-imino-(2-chlorophenylmethyl)-4-(3-carbomethoxy-S-methylisothioureido)benzophenone, m.p. 140°–142° C. (dec.).

Elemental analysis for $C_{24}H_{20}ClN_3O_3S$. Calc.: C, 61.86; H, 4.33; N, 9.02. Found: C, 61.76; H, 4.40; N, 8.80.

EXAMPLE 18

3-Imino-(4-dimethylaminophenylmethyl)-4-(3-carbomethoxy-S-methylisothioureido)benzophenone Step A—3-Imino-(4-dimethylaminophenylmethyl)-4-aminobenzophenone To an ice-cooled solution of 3,4-diaminobenzophenone (8.48 g.; 0.04 mole) in methanol (100 ml.) is added p-N,N-dimethylaminobenzaldehyde (6.0 g.; 0.04 mole). The mixture is stirred at 5° C. for one hour and at room temperature for 18 hours. Sulfuric acid (3 drops) is added to the reaction mixture and within one hour a thick suspension forms. The reaction mixture is stirred at room temperature for an additional 8 hours and the precipitate is collected and dried to afford 10.2 g. of 3-imino-(4-dimethylaminophenylmethyl)-4-aminobenzophenone, m.p. 171°–173° C. (dec.).

Elemental analysis for $C_{22}H_{21}N_3O$. Calc.: C, 76.94; H, 6.16; N, 12.24. Found: C, 76.08; H, 6.17; N, 12.03.

Step B—3-Imino-(4-dimethylaminophenylmethyl)-4-(3-carbomethoxythioureido)benzophenone To a solution of 3-imino-(4-dimethylaminophenylmethyl)-4-aminobenzophenone (9.6 g.; 0.0262 mole) in acetone (2 l.) there is added carbomethoxy isothiocyanate (3.0 g.; 0.0262 mole). The solution is stirred at room temperature for 10 days and the acetone removed under vacuum. The residue is slurried in 100 ml. of acetone and filtered and washed with ether and then dried to afford 8.0 g. of 3-imino-(4-dimethylaminophenylmethyl)-4-(3-carbomethoxythioureido)benzophenone, m.p. 199° C. (dec.).

Elemental analysis for $C_{25}H_{24}N_4O_3S$. Calc.: C, 65.20; H, 5.25; N, 12.17. Found: C, 65.05; H, 5.25; N, 11.98.

Step C—3-Imino-(4-dimethylaminophenylmethyl)-4-(3-carbomethoxy-S-methylisothioureido)benzophenone To a suspension of 3-imino-(4-dimethylaminophenylmethyl)-4-(3-carbomethoxythioureido)benzophenone (3.0 g.; 0.0065 mole) in acetone (50 ml.) and water (10 ml.) there is added an aqueous solution of sodium hydroxide (50%; 0.52 g.). The mixture is stirred at room temperature for one hour and then methyl iodide (0.93 g.) is added. The solution is stirred at room temperature for one hour (a precipitate begins to form after 15 minutes). The precipitate which forms is collected by filtration and dried to afford 0.6 g. of 3-imino-(4-dimethylaminophenylmethyl)-4-(3-carbomethoxy-S-methylisothioureido)benzophenone, m.p. 143°–144° C. (dec.).

Elemental analysis for $C_{22}H_{21}N_3O$. Calc.: C, 76.94; H, 6.16; N, 12.24. Found: C, 76.08; H, 6.17; N, 12.03.

EXAMPLE 19

1-Imino-(p-chlorophenyl)methyl-2-(3-carbomethoxy-S-methylisothioureido)-4-propylthiobenzene Step A—1-Imino-(p-chlorophenyl)methyl-2-(3-carbomethoxythioureido)-4-propylthiobenzene To an ice-cooled solution of 1-amino-2-(3-carbomethoxythioureido)-4-propylthiobenzene (3.0 g.) in absolute methanol (100 ml.) there is added finely divided p-chlorobenzaldehyde (1.4 g.). The yellow solution formed is stirred at 5° C. for one hour (precipitate forms after 10 minutes). The precipitate is collected by filtration. The yellow solid is dried to afford 1.2 g. of 1-imino-(p-chlorophenyl)methyl-2-(3-carbomethoxythioureido)-4-propylthiobenzene, m.p. 170°–172° C. (dec.).

Elemental analysis for $C_{19}H_{20}ClN_3O_2S_2$. Calc.: C, 54.08; H, 4.78; N, 9.96. Found: C, 54.04; H, 4.80; N, 9.89.

Step B—1-Imino-(p-chlorophenyl)methyl-2-(3-carbomethoxy-S-methylisothioureido)-4-propylthiobenzene To a suspension of 1-imino-(p-chlorophenyl)methyl-2-(3-carbomethoxyisothioureido)-4-propylthiobenzene (1.2 g.) in acetone (30 ml.) and water (10 ml.) is added sodium hydroxide (0.23 g.; 50% aqueous). The mixture is stirred at room temperature for one hour and to the solution formed there is added methyl iodide (0.4 g.). A precipitate forms immediately and the suspension is stirred at room temperature for 30 minutes. The precipitate is collected by filtration, washed with ether and dried to afford 1.05 g. of 1-imino-(p-chlorophenyl)- methyl-2-(3-carbomethoxy-S-methylisothioureido)-4-propylthiobenzene, m.p. 139°-140° C.

Elemental analysis for $C_{20}H_{22}ClN_3O_2S_2$. Calc.: C, 55.09; H, 5.09; N, 9.64. Found: C, 54.28; H, 5.06; N, 9.29.

EXAMPLE 20

1-Imino-(2-thienyl)methyl-2-(3-carbomethoxy-S-methylisothioureido)-4-propylthiobenzene Step A—1-Imino-(2-thienyl)methyl-2-(3-carbomethoxythioureido)-4-thiobenzene To an ice-cooled solution of 1-amino-2-(3-carbomethoxythioureido)-4-propylthiobenzene (3.0 g.) in methanol (75 ml.) there is added 2-thiophenecarboxaldehyde (1.12 g.). The solution immediately changes to a yellow color and within 15 minutes a precipitate forms. The suspension is stirred at 5° C. for one hour and at room temperature for 24 hours. The solid is collected by filtration and dried to afford 1.05 g. of 1-imino-(2-thienyl)methyl-2-(3-carbomethoxy-S-methylisothioureido)-4-propylthiobenzene, m.p. 123°-124° C.

Elemental analysis for $C_{17}H_{19}N_3O_2S_3$. Calc.: C, 51.88; H, 4.87; N, 10.68. Found: C, 51.52; H, 4.92; N, 10.63.

Step B—1-Imino-(2-thienyl)methyl-2-(3-carbomethoxy-S-methylisothioureido)-4-propylthiobenzene To a mixture of 1-imino-(2-thienyl)methyl-2-(3-carbomethoxythioureido)-4-propylthiobenzene (1.0 g.) in acetone (20 ml.) and water (7 ml.), there is added a 50% aqueous sodium hydroxide solution (0.203 g.). The mixture is stirred at room temperature for one hour. A solution forms after 15 minutes and to it is added methyl iodide (0.36 g.). The solution is stirred at room temperature for two hours and the precipitate formed is collected by filtration and dried to afford 0.55 g. of 1-imino-(2-thienyl)methyl-2-(3-carbomethoxy-S-methylisothioureido)-4-propylthiobenzene, m.p. 95° C. (dec.).

EXAMPLE 21

1-Imino-(p-chlorophenyl)methyl-2-(3-carbomethoxy-S-methylisothioureido)-4-phenylthiobenzene Step A—1-Imino-(p-chlorophenyl)methyl-2-(3-carbomethoxythioureido)-4-phenylthiobenzene To an ice-cooled solution of 1-amino-2-(3-carbomethoxythioureido)-4-phenylthiobenzene (3.33 g.) in anhydrous methanol (300 ml.) is added finely powdered p-chlorobenzaldehyde (1.4 g.). The solution is stirred at 5° C. for one hour (a precipitate begins to form after 15 minutes). The solid formed is collected by filtration and dried to afford 2.6 g. of 1-imino-(p-chlorophenyl)methyl-2-(3-carbomethoxythioureido)-4-phenylthiobenzene, m.p. 170°-172° C.

Step B—1-Imino-(p-chlorophenyl)methyl-2-(3-carbomethoxy-S-methylisothioureido)-4-phenylthiobenzene To a suspension of 1-imino-(p-chlorophenyl)methyl-2-(3-carbomethoxythioureido)-4-phenylthiobenzene (1.6 g.; 0.00351 mole) in acetone (30 ml.) and water (10 ml.) is added sodium hydroxide (50% aqueous; 0.28 g.). The mixture is stirred at room temperature for one hour and to the solution formed there is added methyl iodide (0.5 g.). A precipitate forms within five minutes and the suspension is stirred at room temperature for 30 minutes. The precipitate is collected and dried to afford 1.02 g. of 1-imino-(p-chlorophenyl)methyl-2-(3-carbomethoxy-S-methylisothioureido)-4-phenylthiobenzene, m.p. 135°-136° C.

Elemental analysis for $C_{23}H_{20}ClN_3O_2S_2$. Calc.: C, 58.77; H, 4.29; N, 8.94. Found: C, 57.90; H, 4.20; N, 8.77.

EXAMPLE 22

3-Imino-(2-thienyl)methyl-4-(3-carbomethoxy-S-methylisothioureido)benzophenone

A mixture of 3-imino-(2-thienyl)methyl-4-(3-carbomethoxythioureido)benzophenone (1.0 g.; 0.0624 mole) in acetone (12 ml.) and water (4 ml.) containing aqueous sodium hydroxide (0.22 g.; 0.0028 mole; 50%) is stirred at room temperature for one hour and methyl iodide (0.4 g.) is added. A precipitate forms almost immediately, filtered and the solid washed with water and dried to afford 0.7 g. of 3-imino-(2-thienyl)methyl-4-(3-carbomethoxy-S-methylisothioureido)benzophenone, m.p. 168°-170° C. (dec.); 67% yield.

EXAMPLE 23

1-Iminophenylmethyl-2-(3-carbomethoxy-S-allylisothioureido)-4-propylthiobenzene

To a suspension of 1-iminophenylmethyl-2-(3-carbomethoxythioureido)-4-propylthiobenzene (1.0 g.) in acetone (30 ml.) and water (10 ml.) there is added aqueous sodium hydroxide (0.21 g.). The mixture is stirred at room temperature for one hour (a solution forms 20 minutes after the addition of sodium hydroxide) and to it there is added allyl bromide (0.36 g.). The solution is stirred at room temperature for two hours and is then poured into water (300 ml.). The mixture is stirred at room temperature for 24 hours and is vacuum filtered. The tacky yellow solid is stirred in hexane (50 ml.) and is filtered to yield 0.35 g. of 1-iminohexylmethyl-2-(3-carbomethoxy-S-isothioureido)-4-propylthiobenzene, m.p. 70°-72° C.

In a manner similar to that described in the written examples, all of the 2-imino substituted thioureidobenzenes (I) of this invention may be prepared by beginning with an appropriately substituted 1,2-diaminobenzene compound and following substantially the procedures described herein. The following equation illustrates the various reactions which may be employed and taken together with Table I, infra, depict the starting materials, intermediates and final products obtained.

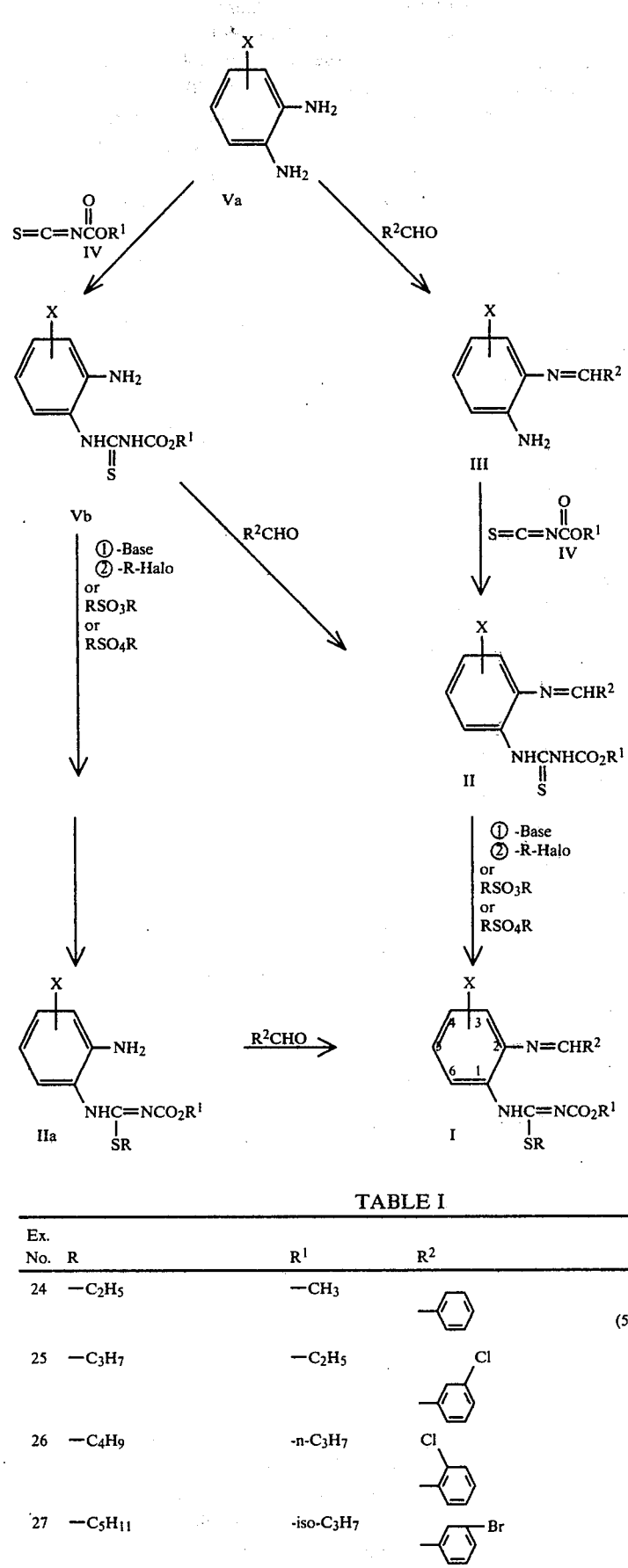
TABLE I
| Ex. No. | R | R¹ | R² | X |
|---|---|---|---|---|
| 24 | —$C_2H_5$ | —$CH_3$ | phenyl | (5) —C(=O)—phenyl |
| 25 | —$C_3H_7$ | —$C_2H_5$ | 3-Cl-phenyl | " |
| 26 | —$C_4H_9$ | -n-$C_3H_7$ | 2-Cl-phenyl | " |
| 27 | —$C_5H_{11}$ | -iso-$C_3H_7$ | 4-Br-phenyl | " |

TABLE I-continued

| Ex. No. | R | R¹ | R² | X |
|---|---|---|---|---|
| 28 | —C$_6$H$_{13}$ | -n-C$_4$H$_9$ |  (Br-phenyl) | " |
| 29 | —C$_7$H$_{15}$ | -iso-C$_4$H$_9$ |  (Br-phenyl) | " |
| 30 | —C$_8$H$_{17}$ | -tert-C$_4$H$_9$ |  (CH$_3$-phenyl) | " |
| 31 | —(CH$_2$)$_2$CH=CH$_2$ | cyclo-C$_5$H$_9$ |  (CH$_3$-phenyl) | " |
| 32 | —(CH$_2$)$_3$CH=CH$_2$ | cyclo-C$_5$H$_9$ |  (CH$_3$-phenyl) | " |
| 32 | —(CH$_2$)$_3$CH=CH$_2$ | cyclo-C$_6$H$_{11}$ |  (CH$_3$-phenyl) | " |
| 33 | —(CH$_2$)$_4$CH=CH$_2$ | —CH$_3$ |  (C$_2$H$_5$-phenyl) | " |
| 34 | —(CH$_2$)$_5$CH=CH$_2$ | —CH$_3$ |  (C$_2$H$_5$-phenyl) | " |
| 35 | —(CH$_2$)$_6$CH=CH$_2$ | —CH$_3$ |  (C$_2$H$_5$-phenyl) | " |
| 36 | —CH$_2$C≡CH | —CH$_3$ |  (naphthyl) | " |
| 37 | —(CH$_2$)$_2$C≡CH | —CH$_3$ |  (thienyl) | " |
| 38 | —(CH$_2$)$_3$C≡CH | —CH$_3$ |  (pyridyl) | (5) —$\overset{O}{\overset{\|}{C}}$CH$_3$ |
| 39 | —(CH$_2$)$_4$C≡CH | —CH$_3$ |  (phenyl) | (5) —$\overset{O}{\overset{\|}{C}}$C$_2$H$_5$ |
| 40 | —(CH$_2$)$_5$C≡CH | —CH$_3$ |  (phenyl) | (5) —$\overset{O}{\overset{\|}{C}}$C$_3$H$_7$ |
| 41 | —(CH$_2$)$_6$C≡CH | —CH$_3$ |  (NO$_2$-phenyl) | (5) —$\overset{O}{\overset{\|}{C}}$C$_4$H$_9$ |
| 42 | —CH$_2$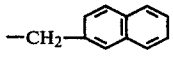 | —C$_2$H$_5$ |  (NO$_2$-phenyl) | (5) —OCH$_3$ |
| 43 | —CH$_2$CH$_2$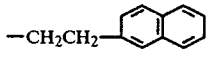 | —C$_2$H$_5$ |  (O$_2$N-phenyl) | (4) —OC$_2$H$_5$ |
| 44 | —CH$_2$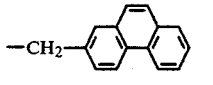 | —CH$_3$ |  (O$_2$N-phenyl) | (4) —OC$_3$H$_7$ |
| 45 | —CH$_2$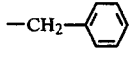 | —C$_3$H$_7$ |  (NO$_2$-phenyl) | (4) —OC$_4$H$_9$ |
| 46 | —CH$_2$CH$_2$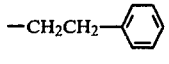 | —CH$_3$ |  (CN-phenyl) | (4) —OC$_5$H$_9$ |
| 47 | —CH$_2$CH$_2$CH$_2$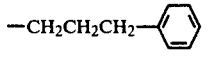 | -tert-C$_4$H$_9$ |  (NC-phenyl) | (5) —SCN |

TABLE I-continued

| Ex. No. | R | R$^1$ | R$^2$ | X |
|---|---|---|---|---|
| 48 | —CH$_2$—C$_6$H$_4$—Cl | -tert-C$_4$H$_9$ | —C$_6$H$_4$—OCH$_3$ | (5) —SO—C$_6$H$_5$ |
| 49 | —CH$_2$—C$_6$H$_4$—CH$_3$ | —CH$_3$ | —C$_6$H$_4$—OCH$_3$ | (5) —SO$_2$—C$_6$H$_5$ |
| 50 | —CH$_2$CH$_2$—C$_6$H$_4$—OCH$_3$ | —CH$_3$ | —C$_6$H$_4$(CH$_3$CO)— | (4) —O—SO$_2$—C$_6$H$_5$ |
| 51 | —(CH$_2$)$_3$—O—C$_6$H$_5$ | —CH$_3$ | —C$_6$H$_4$(CH$_3$CO)— | (5) —O—SO$_2$—C$_6$H$_5$ |
| 52 | —(CH$_2$)$_4$—O—C$_6$H$_5$ | —CH$_3$ | —C$_6$H$_5$ | (4) —SCH$_3$ |
| 53 | —(CH$_2$)$_5$—O—C$_6$H$_5$ | cyclo-C$_5$H$_9$ | —C$_6$H$_4$—F | (4) —SC$_3$H$_7$ |
| 54 | —(CH$_2$)$_6$—O—C$_6$H$_5$ | cyclo-C$_5$H$_9$ | —C$_6$H$_4$—CH$_3$ | (5) —SOC$_3$H$_7$ |
| 55 | —CH$_2$—cyclo-C$_5$H$_9$ | -n-C$_3$H$_7$ | —C$_6$H$_4$—CF$_3$ | (5) —SO$_2$CH$_3$ |
| 56 | —(CH$_2$)$_2$—cyclo-C$_5$H$_9$ | -n-C$_3$H$_7$ | -n-C$_3$H$_7$ | (5) —SO$_2$C$_3$H$_7$ |
| 57 | —CH$_2$—cyclo-C$_6$H$_{11}$ | —CH$_3$ | -n-C$_4$H$_9$ | (4) —NHC(O)CH$_3$ |
| 58 | —(CH$_2$)$_2$—cyclo-C$_6$H$_{11}$ | —C$_2$H$_5$ | -n-C$_5$H$_{11}$ | (5) —NHC(O)—cyclo-C$_5$H$_9$ |
| 59 | —(CH$_2$)$_3$CN | —CH$_3$ | -n-C$_5$H$_{11}$ | (4) —NHC(O)—cyclo-C$_6$H$_{11}$ |
| 60 | —(CH$_2$)$_4$CN | —CH$_3$ | —C$_6$H$_{10}$—Cl (cyclohexyl) | (4) —NHC(O)—OC$_2$H$_5$ |
| 61 | —(CH$_2$)$_5$CN | —CH$_3$ | —C$_6$H$_5$ | (5) —NHC(O)—O—CH(CH$_3$)$_2$ |
| 62 | —(CH$_2$)$_6$CN | —CH$_3$ | " | (4) —NHC(O)—OC$_4$H$_9$ |
| 63 | —(CH$_2$)$_3$OH | " | " | (5) —C(O)—C$_6$H$_5$ |
| 64 | —(CH$_2$)$_4$OH | " | —C$_6$H$_4$—Cl | (4) —S—C$_6$H$_5$ |
| 65 | —(CH$_2$)$_5$OH | " | —C$_6$H$_5$ | (5) —SO—C$_6$H$_5$ |
| 66 | —(CH$_2$)$_8$OH | " | " | (5) —SO$_2$—C$_6$H$_5$ |
| 67 | —CH=CHCH$_2$—C$_6$H$_5$ | " | " | (5) —C(O)—C$_6$H$_4$—Cl |
| 68 | —(CH$_2$)$_3$OCH$_3$ | " | " | (5) —C(O)—C$_6$H$_4$—OCH$_3$ |
| 69 | —(CH$_2$)$_3$OC$_2$H$_5$ | " | " | (5) —C(O)—C$_6$H$_4$—CH$_3$ |

TABLE I-continued

| Ex. No. | R | R¹ | R² | X |
|---|---|---|---|---|
| 70 | —(CH₂)₄OCH₃ | —CH₃ | " | (5) —C(O)—C₆H₄—CF₃ (meta) |
| 71 | —(CH₂)₄OC₃H₇ | —C₃H₇ | " | (5) —C(O)—C₆H₄—CF₃ (para) |
| 72 | —(CH₂)₃C(O)—OCH₃ | —C₂H₅ | " | (5) —C(O)—C₆H₅ |
| 73 | —(CH₂)₄C(O)OC₂H₅ | —C₂H₅ | 4-Cl-C₆H₄— | (5) —C(O)—C₆H₅ |
| 74 | —(CH₂)₅C(O)OC₂H₅ | " | " | (4) —SO—C₆H₄—Cl |
| 75 | —(CH₂)₆C(O)—OC₃H₇ | —C₃H₇ | " | (4) —SO—C₆H₄—C(O)CH₃ |
| 76 | —(CH₂)₄-N(phthalimido) | —CH₃ | " | (4) —SO₂—C₆H₄—CN |
| 77 | —(CH₂)₃C(O)—O—C₆H₅ | " | " | (4) —SO₂—C₆H₄—C(O)CH₃ |
| 78 | —(CH₂)₄C(O)—O—C₆H₅ | " | " | (4) —S—C₆H₄—CN |
| 79 | —(CH₂)₅C(O)—O—C₆H₅ | " | " | " |
| 80 | —(CH₂)₆C(O)—O—C₆H₅ | " | " | (5) —C₄H₉-n |
| 81 | —C₄H₉ | " | 2-pyrrolyl (NH) | H |
| 82 | —C₃H₇ | —C₂H₅ | 2-pyrrolyl (NH) | (4) —C(O)—C₆H₅ |
| 83 | —C₂H₅ | —C₃H₇ | 2-thiazolyl | " |
| 84 | —CH₃ | —C₄H₉ | 1,3,4-oxadiazol-2-yl | " |
| 85 | —C₄H₉ | —C₃H₇ | 1,3,4-thiadiazol-2-yl | " |
| 86 | —C₃H₇ | —C₂H₅ | 2-pyridyl | (5) —C(O)—C₆H₅ |
| 87 | —C₂H₅ | —CH₃ | 3-isoxazolyl | H |
| 88 | —CH₃ | —CH₃ | 3-pyridyl | H |
| 89 | —C₄H₉ | —C₂H₅ | 1-methyl-2-pyrrolyl | H |

TABLE I-continued

| Ex. No. | R | $R^1$ | $R^2$ | X |
|---|---|---|---|---|
| 90 | $-C_4H_9$ | $n-C_4H_9$ | (furyl-O-CH= fused pyrimidine structure) | H |
| 91 | $-C_3H_7$ | $tert-C_4H_9$ | (pyrimidine structure) | (5) $-C_3H_7$ |
| 92 | $-CH_3$ | $tert-C_4H_9$ | (pyrimidine structure) | (4) $-C_4H_9$ |
| 93 | $-C_4H_9$ | $tert-C_4H_9$ | (pyridyl structure) | (4) $-C_2H_5$ |

EXAMPLE 94

1-Imino(2-furylmethyl)-2-(3-carbomethoxy-S-benzylisothioureide)benzene

To 100.0 g (0.33 mole) of imino(2-furylmethyl)-2-(3-carbomethoxythioureido) benzene and 50.0 g. (0.395 mole) of benzyl chloride in 275 ml. of dimethyl sulfoxide is slowly added 15.0 g (0.375 mole) of sodium hydroxide in 260 g. of water. The resulting mixture is stirred for ½ hour and the yellow precipitate is separated by filtration and recrystallized from 800 ml of methylene chloride-hexane (1:1) to give 91.1 g (70.1%) of 1-imino-(2-furylmethyl)-2-(3-carbomethoxy-S-benzylisothioureido)benzene m.p. 112°–114° C.

Elemental Analysis for $C_{21}H_{19}NOS$: Calc: C, 64.10; H, 4.87; N, 10.68; O, 12.20; S, 8.15. Found: C, 64.22; H, 4.83; N, 11.11; 0, 12.29; S, 8.24.

EXAMPLE 95

1-Imino)2-furylmethyl)-2-(3-carbomethoxy-S-butylisothioureido)benzene

To 5.0 g (0.0165 mole) of 1-imino(2-furylmethyl)-2-(3-carbomethoxythioureido)benzene and 3.6 g (0.01975 mole) of iodobutane in 80 ml. of N,N-dimethylformamide is added 0.7 g (0.0175 mole) of sodium hydroxide in 20 ml of water. The resulting mixture is stirred for ½ hour and the yellow precipitate that formed is separated by filtration, washed with 50 ml of water and dried to give 3.4 g of crude product, m.p. 86°–7° C. Recrystallization from ether-hexane affords 1-imino(2-furylmethyl)-2-(3-carbomethoxy-S-butylisothioureido)benzene m.p. 84°–85° C.

Elemental Analysis for $C_{18}H_{21}N_3O_3S$: Calc.: C, 60.15; H, 5.89; N, 11.69; O, 13.35; S, 8.92. Found: C, 59.98; H, 5.93; N, 11.77; O, 13.83; S, 8.90.

EXAMPLE 96

1-Imino(2-furylmethyl)-2-(3-carbomethoxy-S-methylisothioureido)benzene

A mixture of 3.03 g (0.01 mole) 1-imino(2-furylmethyl)-2-(3-carbomethoxythioureido)benzene, 1.38 g (0.01 mole) of potassium carbonate, and 1.42 g (0.01 mole) of methyl iodide in 50 ml of acetone is refluxed and stirred for 1 hour. The suspension is allowed to stand at room temperature for 24 hours and is vacuum filtered. The filtrate is concentrated in vacuo and the residue orange semi-solid is slurried in 50 ml of ether and allowed to stand at room temperature for 24 hours. The suspension formed is vacuum filtered and the filter cake of gold needles is dried to afford 2.45 g (77% yield) of product, m.p. 97°–105° C.

A sample of the product recrystallized from ether affords 1-imino(2-furylmethyl)2-(3-carbomethoxy-S-methylisothioureido)benzene as a fluffy yellow solid, m.p. 94°–97° C.

Elemental Analysis for $C_{15}H_{15}N_3O_3S$: Calc: C, 56.77; H, 4.76; N, 13.24; S, 10.10. Found: C, 57.22; H, 4.84; N, 13.60; S, 10.43.

EXAMPLE 97

1-Imino-(p-chlorophenyl)methyl-2-(3-carbomethoxy-S-methylisothioureido)-4-propylthiobenzene To a mixture of 1-imino-(p-chlorophenyl)-methyl-2-(3-carbomethoxythioureido)-4-propylthiobenzene (4.22 g.; 0.01 mol) in acetone (25 ml.) and water (10 ml.) there is added 50% aqueous sodium hydroxide (0.8 g.; 0.01 mol). The mixture is stirred at room temperature for one hour and to it there is added dimethyl sulfate (1.26 g.; 0.01 mol). The reaction mixture is stirred at room temperature for one hour and the precipitate collected and dried to afford 1-imino-(p-chlorophenyl)methyl-2-(3-carbomethoxy-S-methylisothioureido)-4-propylthiobenzene.

EXAMPLE 98

1-Iminophenylmethyl-2-(3-carbomethoxy-S-methylisothioureido)-4-propylthiobenzene To a solution of 1-iminophenylmethyl-2-(3-carbomethoxythioureido)-4-propylthiobenzene (3.88 g.; 0.01 mol) in acetone (40 ml.) and water (10 ml.) there is added calcium hydroxide (0.74 g.; 0.01 mol). The mixture is stirred at room temperature for 4 hours and then is added methyl iodide (1.42 g.; 0.01 mol). The mixture is stirred at room temperature for 4 hours and the precipitate collected and dried to afford 1-iminophenylmethyl-2-(3-carbomethoxy-S-methylisothioureido)-4-propylthiobenzene.

EXAMPLE 99

1-Iminophenylmethyl-2-(3-carbomethoxy-S-methylisothioureido)-4-propylthiobenzene To a solution of 1-iminophenylmethyl-2-(3-carbomethoxythioureido)-4-propylthiobenzene (3.88 g.; 0.01 mol) in dimethylformamide (40 ml.) and water (10 ml.) there is added calcium hydroxide (0.74 g.; 0.01 mol). The mixture is stirred at room temperature for four hours and to it there is added dimethylsulfate (1.26 g.). The mixture is stirred at room temperature for four hours and the precipitate collected and dried to afford 1-iminophenylmethyl-2-(3-carbomethoxy-S-methylisothioureido)-4-propylthiobenzene.

EXAMPLE 100

1-Imino-(o-chlorophenyl)methyl-2-(3-carbomethoxy-S-methylisothioureido)-4-propylthiobenzene To a mixture of 1-imino-(o-chlorophenyl)methyl-2-(3-carbomethoxythioureido)-4-propylthiobenzene (4.22 g.; 0.01 mol) in acetone (25 ml.) and water (10 ml.) there is added 50% aqueous sodium hydroxide (0.8 g.; 0.01 mol). The mixture is stirred at room temperature for one hour and there is then added dimethyl sulfite (1.1 g.; 0.01 mol). The mixture is stirred at room temperature for 3 hours and the precipitate collected and dried to afford 1-imino-(o-chlorophenyl)-methyl-2-(3-carbomethoxy-S-methylisothioureido)-4-propylthiobenzene.

EXAMPLE 101

1-Iminophenylmethyl-2-(3-carbomethoxy-S-methylisothioureido)-5-benzoylbenzene

To a solution of 1-iminophenylmethyl-2-(3-carbomethoxythioureido)-5-benzoylbenzene (4.33 g.; 0.01 mol) in dimethylformamide (50 ml.) and water (5 ml.) there is added calcium hydroxide (0.74 g.; 0.01 mol). The mixture is stirred at 30° C. for 2 hours and to it there is added dimethyl sulfite (1.1 g.; 0.01 mol). The mixture is stirred at room temperature for 3 hours and the precipitate collected and dried to afford 1-iminophenylmethyl-2-(3-carbomethoxy-S-methylisothioureido)-5-benzoylbenzene.

EXAMPLE 102

1-Imino-(p-chlorophenyl)methyl-2-(3-carbomethoxy-S-methylisothioureido)-4-phenylthiobenzene To a mixture of 1-imino-(p-chlorophenyl)-methyl-2-(3-carbomethoxythioureido)-4-phenylthiobenzene (4.56 g.; 0.01 mol) in acetone (35 ml.) there is added 57% sodium hydride (0.42 g.; 0.01 mol) (oil dispersion). The mixture is stirred at room temperature for one hour and there is then added methyl iodide (1.42 g.; 0.01 mol). The mixture is stirred at room temperature for one hour and is poured into an excess of water. The suspension is filtered and the precipitate dried to afford 1-imino-(p-chlorophenyl)methyl-2-(3-carbomethoxy-S-methylisothioureido)-4-phenylthiobenzene.

EXAMPLE 103

3-Imino-(o-chlorophenyl)methyl-4-(3-carbomethoxy-S-methylisothioureido)benzophenone To a mixture of 3-imino-(o-chlorophenyl)methyl-4-(3-carbomethoxythioureido)benzophenone (4.52 g.; 0.01 mol) in 1,2-dimethoxyethane (50 ml.) there is added 57% sodium hydride (0.42 g.; 0.01 mol) (oil dispersion). The mixture is stirred at room temperature for one hour and there is then added dimethyl sulfate (1.26 g.; 0.01 mol). The mixture is stirred at room temperature for one hour and is poured into an excess of water. The suspension is filtered and the filter cake dried to afford 3-imino-(o-chlorophenyl)methyl-4-(3-carbomethoxy-S-methylisothioureido)benzophenone.

EXAMPLE 104

3-Imino-(o-nitrophenyl)methyl-4-(3-carbomethoxy-S-methylisothioureido)benzophenone To a mixture of 3-imino-(o-nitrophenyl)methyl-4-(3-carbomethoxythioureido)benzophenone (4.62 g.; 0.01 mol) in dimethyl formamide (40 ml.) there is added 57% sodium hydride (0.42 g.; 0.01 mol) (oil dispersion). The mixture is stirred at room temperature for one hour and to it there is added dimethyl sulfite (1.1 g.; 0.01 mol). The mixture is stirred at room temperature for 1½ hours and is poured into an excess of water. The suspension formed is vacuum filtered and the filter caked dried to afford 3-imino-(o-nitrophenyl)methyl-4-(3-carbomethoxy-S-methylisothioureido)benzophenone.

EXAMPLE 105

3-Imino-(3,4-dichlorophenyl)methyl-4-(3-carbomethoxy-S-methylisothioureido)benzophenone To a mixture of 3-imino-(3,4-dichlorophenyl)-methyl-4-(3-carbomethoxythioureido)benzophenone (4.86 g.; 0.01 mol) in acetone (50 ml.) there is added calcium hydride (0.42 g.; 0.01 mol). The mixture is refluxed for one hour and then cooled to room temperature. To the mixture is added methyl iodide (1.42 g.; 0.01 mol). The mixture is stirred at room temperature for one hour and is poured into an excess of ice water. The suspension formed is filtered and the filter cake dried to afford 3-imino-(3,4-dichlorophenyl)methyl-4-(3-carbomethoxy-S-methylisothioureido)benzophenone.

EXAMPLE 106

3-Imino-(4-methoxyphenyl)methyl-4-(3-carbomethoxy-S-methylisothioureido)benzophenone To a mixture of 3-imino-(4-methoxyphenyl)methyl-4-(3-carbomethoxythioureido)benzophenone (4.47 g.; 0.01 mol) in 1,2-dimethoxyethane (50 ml.) there is added calcium hydride (0.42 g.; 0.01 mol). The mixture is refluxed for one hour and is cooled to room temperature. To the mixture there is added dimethylsulfate (1.26 g.; 0.01 mol). The mixture is stirred at room temperature for one hour and is poured into an excess of ice water. The suspension formed is filtered and the filter cake dried to afford 3-imino-(4-methoxyphenyl)methyl-4-(3-carbomethoxy-S-methylisothioureido)benzophenone.

EXAMPLE 107

3-Imino-(4-nitrophenyl)methyl-4-(3-carbomethoxy-S-methylisothioureido)benzophenone To a mixture of 3-imino-(4-nitrophenyl)-methyl-4-(3-carbomethoxythioureido)benzophenone (4.62 g.; 0.01 mol) in acetone (50 ml.) there is added calcium hydride (0.42 g.; 0.01 mol). The mixture is refluxed for one hour and is cooled to room temperature. To the mixture there is added dimethylsulfite (1.1 g.; 0.01 mol). The mixture is stirred at room temperature for one hour and is poured into an excess of ice water. The suspension formed is filtered and the filter cake dried to afford 3-imino-(4-nitrophenyl)methyl-4-(3-carbomethoxy-S-methylisothioureido)benzophenone.

EXAMPLE 108

1-Iminophenylmethyl-2-(3-carbomethoxy-S-methylisothioureido)-4-propylthiobenzene To a mixture of 2-(3-carbomethoxy-S-methylisothioureido)-4-propylthioaniline (3.13 g.; 0.01 mol) in methanol (25 ml.), cooled to 5° C., there is added benzaldehyde (1.06 g.; 0.1 mol). The mixture is stirred at room temperature for one hour and is filtered. The filter cake is dried to afford 1-iminophenylmethyl-2-(3-carbomethoxy-S-methylisothioureido)-4-propylthiobenzene.

EXAMPLE 109

1-Imino-(4-chlorophenyl)methyl-2-(3-carbomethoxy-S-methylisothioureido)-4-phenylthioaniline To a mixture of 2-(3-carbomethoxy-S-methylisothioureido)-4-phenylthioaniline (4.56 g.; 0.01 mol) in methanol (25 ml.), cooled to 5° C., is added p-chlorobenzaldehyde (1.4 g.; 0.01 mol) followed by concentrated sulfuric acid (3 drops). The mixture is stirred at 5° C. for one hour and is then vacuum filtered. The filter cake is dried to afford 1-imino-(4-chlorophenyl)methyl-2-(3-carbomethoxy-S-methylisothioureido)-4-phenylthioaniline.

EXAMPLE 110

3-Imino-(4-nitrophenyl)methyl-4-(3-carbomethoxy-S-methylisothioureido)benzophenone To a mixture of 3-amino-4-(3-carbomethoxy-S-methylisothioureido)benzophenone (3.43 g.; 0.01 mol) in benzene (100 ml.) there is added 4-nitrobenzaldehyde (1.5 g.; 0.01 mol). The mixture is refluxed and stirred for 3 hours. Water of the reaction is removed by a Dean-Stark distillation receiver. The mixture is poured into an excess of hexane and the suspension formed is vacuum filtered. The filter cake is dried to afford 3-imino-(4-nitrophenyl)methyl-4-(3-carbomethoxy-S-methylisothioureido)benzophenone.

EXAMPLE 111

3-Imino-(4-methoxyphenyl)methyl-4-(3-carbomethoxy-S-methylisothioureido)benzophenone To a mixture of 3-amino-4-(3-carbomethoxy-S-methylisothioureido)benzophenone (3.43 g.; 0.01 mol) in benzene (100 ml.) there is added p-methoxybenzaldehyde (1.36 g.; 0.01 mol) and p-toluenesulfonic acid monohydrate (0.1 g.). The mixture is refluxed and stirred for 3 hours. The water reaction is removed by a Dean-Stark distillation receiver. The mixture is poured into an excess of hexane and the suspension formed is filtered. The filter cake is dried to afford 3-imino-(4-methoxyphenyl)methyl-4-(3-carbomethoxy-S-methylisothioureido)benzophenone.

EXAMPLE 112

1-Iminophenylmethyl-2-(3-carbomethoxy-S-methylisothioureido)-4-n-propylsulfinylbenzene To a solution of 1-iminophenylmethyl-2-(3-carbomethoxy-S-methylisothioureido)-4-n-propylthiobenzene (4.02 g.; 0.01 mol) in methylene chloride (50 ml.), cooled to −5° C., is added 85% of m-chloroperoxybenzoic acid (2.02 g.; 0.01 mol). The mixture is stirred at −5° C. for 30 minutes and is washed with aqueous sodium bicarbonate solution. The methylene dichloride is evaporated from the organic solution to afford 1-iminophenylmethyl-2-(3-carbomethoxy-S-methylisothioureido)-4-n-propylsulfinylbenzene.

EXAMPLE 113

1-Iminophenylmethyl-2-(3-carbomethoxy-S-methylisothioureido)-4-n-propylsulfonylbenzene To a solution of 1-iminophenylmethyl-2-(3-carbomethoxy-S-methylisothioureido)-4-n-propylthiobenzene (4.02 g.; 0.01 mol) in methylene chloride (50 ml.), cooled to −5° C., is added m-chloroperoxybenzoic acid (4.04 g.; 0.02 mol). The mixture is stirred at room temperature for 2 hours and is washed with aqueous sodium bicarbonate solution. The methylene dichloride is evaporated from the organic mixture to afford 1-iminophenylmethyl-2-(3-carbomethoxy-S-methylisothioureido)-4-n-propylsulfonylbenzene.

EXAMPLE 114

1-Iminopropyl-2-(3-carbomethoxy-S-methylisothioureido)-4-propylthiobenzene

Step A—1-Iminopropyl-2-(3-carbomethoxythioureido)-4-propylthiobenzene

To a suspension of 2-(3-carbomethoxythioureido)-4-propylthioaniline (2.99 g.; 0.01 mole) in methanol (50 ml.), cooled to 5° C., there is added propionaldehyde (0.64 g.; 0.01 mole). The mixture is stirred at 5° C. for 2 hours and the solution formed is stirred at room temperature for 1 week. The suspension that forms is vacuum filtered and the filter cake is washed with ether and dried to afford 1-imino propyl-2-(3-carbomethoxythioureido)-4-propylthiobenzene (1.3 g.; 38.3%), m.p. 163°–168° C. (dec.).

Elemental analysis for $C_{15}H_{21}N_3O_2S_2$. Calc.: C, 53.07; H, 6.24; N, 12.38. Found: C, 52.72; H, 6.32; N, 12.38.

Step B—1-Iminopropyl-2-(3-carbomethoxy-S-methylisothioureido)-4-propylthiobenzene To a suspension of 1-iminopropyl-2-(3-carbomethoxythioureido)-4-propylthiobenzene (1 g.; 0.00295 mole) in acetone (30 ml.) and water (15 ml.) there is added 50.8% aqueous sodium hydroxide (0.23 g.; 0.00295 mole). The solution that forms is stirred at room temperature for one hour and to it there is added methyl iodide (0.42 g.; 0.00295 mole). The turbid solution formed is stirred at room temperature for 30 minutes and is poured into water (500 ml.). The suspension formed is stirred at room temperature for one hour and is vacuum filtered. The filter cake is dried to afford 1-iminopropyl-2-(3-carbomethoxy-S-methylisothioureido)-4-propylthiobenzene (0.85 g.; 81.5%), m.p. 85°–90° C. (dec.).

Elemental analysis for $C_{16}H_{23}N_3O_2S_2$. Calc.: C, 54.36; H, 6.56; N, 11.89. Found: C, 53.96; H, 6.60; N, 11.63.

EXAMPLE 115

1-Imino (4-methyl)phenylmethyl-2-(3carbomethoxy-S-methylisothioureido)-4-propylthiobenzene Step A—1-Imino(4-methyl)phenylmethyl-2-(3-carbomethoxythioureido-4-propylthiobenzene To a suspension of 2-(3-carbomethoxythioureido)-4-propylthioaniline (9.0 g; 0.03 mole) in methanol (100 ml), cooled to 10° C., there is added p-methylbenzaldehyde (3.6 g; 0.03 mole). The mixture is stirred at 10° C. for 1 hr. and at room temperature for 18 hrs. The suspension that forms is vacuum filtered and the filter cake is air dried to afford 1-imino(4-methyl)phenylmethyl-2-(3-carbomethoxythioureido)-4-propylthiobenzene (10.75 g; 89%), m.p. 135°–141° C.

Elemental Analysis for $C_{20}H_{23}N_3O_2S_2$. Calc: C, 59.82; H, 5.77; N, 10.46. Found: C, 59.32; H, 5.87; N, 10.75.

Step B—1-Imino(4-methyl)phenylmethyl-2-(3-carbomethoxy-S-methylisothioureido)-4-propylthiobenzene To a suspension of 1-imino(4-methyl)phenylmethyl-2-(3-carbomethoxythioureido)-4-propylthiobenzene (4.02 g; 0.01 mole) in acetone (60 ml) and water (20 ml) there is added 50% aqueous sodium hydroxide (0.8 g; 0.01 mole). The solution that forms within 10 min. is stirred at room temperature for 50 min. and to it there is added methyl iodide (1.42 g; 0.01 mole). The suspension that forms is stirred at room temperature for 1 hr. and is vacuum filtered. The filter cake is air dried to afford 1-imino(4-methyl)phenylmethyl-2-(3-carbomethoxy-S-methyl isothioureido)-4-propylthiobenzene (3.6 g; 86.6%), m.p. 113°–115° C.

Elemental analysis for $C_{21}H_{25}N_3O_2S_2$. Calc: C, 60.69; H, 6.06; N, 10.11. Found: C, 60.75; H, 6.29; N, 10.47.

EXAMPLE 116

1-Imino-(4-methoxy)phenylmethyl-2-(3-carbomethoxy-S-methylisothioureido)-4-propylthiobenzene Step A—1-Imino-(4-methoxy)phenylmethyl-2-(3-carbomethoxythioureido)-4-propylthiobenzene To a suspension of 2-(3-carbomethoxy thioureido)-4-propylthioaniline (9.0 g; 0.03 mole) in methanol (100 ml) cooled to 10° C., there is added p=anisaldehyde (4.08 g; 0.03 mole). The mixture is stirred at 10° C. for 1 hr. and at room temperature for 18 hrs. The suspension that forms is vacuum filtered and the filter cake air dried to afford 1-imino-(4-methoxy)phenylmethyl-2-(3-carbomethoxythioureido)-4-propylthiobenzene (9.9 g.; 79%), m.p. 141°–144° C.

Elemental analysis for $C_{20}H_{23}N_3O_3S_2$. Calc: C, 57.53; H, 5.55; N, 10.06. Found: C, 57.19; H, 5.67; N, 10.25.

Step B—1-Imino-(4-methoxy)phenylmethyl-2-(3-carbomethoxy-S-methylisothioureido)-4-propylthiobenzene To a suspension of 1-imino-(4-methoxy)phenylmethyl-2-(3-carbomethoxythioureido)-4-propylthiobenzene (4.18 g; 0.01 mole) in acetone (60 ml) and water (20 ml) there is added 50% aqueous sodium hydroxide (0.08 g; 0.01 mole). The solution that forms within 10 min. is stirred at room temperature for 50 min. and to it there is added methyl iodide (1.42 g; 0.01 mole). The suspension that forms is stirred at room temperature for 1 hr. and is vacuum filtered. The filter cake is air dried to afford 1-imino-(4-methoxy)phenylmethyl-2-(3-carbomethoxy-S-methylisothioureido)-4-propylthiobenzene (2.3 g; 53%), m.p. 90–92.

Elemental analysis for $C_{21}H_{25}N_3O_3S_2$. Calc: C, 58.44; H, 5.84; N, 9.74. Found: C, 58.38; H, 5.94; N, 9.91.

EXAMPLE 117

1-Imino(4-nitro)phenylmethyl-2-(3-carbomethoxy-S-methylisothioureido)-4-propylthiobenzene Step A—1-Imino-(4-nitro)phenylmethyl-2-(3-carbomethoxythioureido)-4-propylthiobenzene To a suspension of 2-(3-carbomethoxythioureido)-4-propylthioaniline (4.0 g; 0.013 mole) in methanol (35 ml) there is added a solution of p-nitrobenzaldehyde (2.0 g; 0.013 mole) in methanol (35 ml). The mixture is stirred at room temperature for 1 hr. and is vacuum filtered. The filter cake is washed with methanol and dried to afford 1-imino(4-nitro)phenylmethyl-2-(3-carbometoxythioureido)-4-propylthiobenzene (5.3 g; 94%), m.p. 198°–200° C.

Elemental analysis for $C_{19}H_{20}N_4O_4S_2$. Calc: C, 52.76; H, 4.66; N, 12.95; S, 14.83. Found: C, 52.85; H, 4.79; N, 13.39; S, 14.84.

Step B—1-Imino-(4-nitro)phenylmethyl-2-(3-carbomethoxy-S-methylisothioureido)-4-propylthiobenzene A mixture of 1-imino-(4-nitro)phenylmethyl-2-(3-carbomethoxythioureido)-4-propylthiobenzene (4.3 g; 0.01 mole) acetone (50 ml), water (25 ml) and 50% aqueous sodium hydroxide (0.8 g; 0.01 mole) is stirred at room temperature for 15 min. and is cooled to 12° C. To the mixture there is added methyl iodide (1.4 g; 0.01 mole) and it is stirred at 13° C. to 20° C. for 2 hrs. The suspension that forms is vacuum filtered and the filter cake is washed with acetone and dried to afford 1-imino(4-nitro)phenylmethyl-2-(3-carbomethoxy-S-methylisothioureido)-4-propylthiobenzene (3.5 g; 78%), m.p. 135°–137° C. dec.

Elemental analysis for $C_{20}H_{22}N_4O_4S_2$. Calc: C, 53.79; H, 4.97; N, 12.55; S, 14.36. Found: C, 53.39; H, 4.97; N, 12.60; S, 14.69.

EXAMPLE 118

1-Imino-(2-furylmethyl)-2-(3-carbomethoxy-S-methylisothioureido)-4-propylthiobenzene Step A—1-Imino-(2-furylmethyl)-2-(3-carbomethoxythioureido)-4-propylthiobenzene To a suspension of 2-(3-carbomethoxythioureido)-4-propylthioaniline (6.0 g; 0.02 mole) in methanol (200 ml), cooled to 10° C. there is added 2-furfuraldehyde (1.92 g, 0.02 mole). The mixture is stirred at 10° C. for 1 hr. and at room temperature for 18 hrs. The suspension formed is vacuum filtered and the filter cake is air dried to afford 1-imino(2-furylmethyl)-2-(3-carbomethoxythiouriedo)-4-propylthioaniline (5.6 g; 74%), m.p. 131°–133° C.

Elemental analysis for $C_{17}H_{19}N_3O_3S_2$. Calc: C, 54.09; H, 5.07; N, 11.13. Found: C, 53.68; H, 5.11; N, 11.13.

Step B—1-Imino-(2-furylmethyl)-2-(3-carbomethoxy-S-methylisothioureido)-4-propylthiobenzene To a suspension of 1-imino-(2-furylmethyl)-2-(3-carbomethoxythioureido)-4-propylthiobenzene (3.77 g; 0.01 mole) in acetone (45 ml) and water (15 ml) there is added 50% aqueous sodium hydroxide (0.79 g; 0.01 mole). Within 15 min. after addition a solution forms and is stirred at room temperature for 30 min. To the solution there is added methyl iodide (1.42 g; 0.01 mole). The mixture is stirred at room temperature for 1¾ hrs. and the suspension that forms is vacuum filtered. The filter cake is air dried to afford 1-imino-(3-furylmethyl)-2-(3-carbomethoxy-S-methylisothioureido)-4-propylthiobenzene (2.65 g; 67.7%), m.p. 96°–98° C.

Elemental analysis for $C_{18}H_{21}N_3O_3S_2$. Calc: C, 55.22; H, 5.41; N, 10.73. Found: C, 54.71; H, 5.39; N, 10.51.

EXAMPLE 119

When the procedures of the above examples are followed and by employing known starting diamine precursors, the following products may be obtained:
3-iminophenylmethyl-4-(3-carboethoxy-S-methylisothioureido)-benzophenone;

3-imino(p-chloro)phenylmethyl-4-(3-carbopropoxy-S-methylisothioureido)benzophenone;
1-iminophenylmethyl-2-(3-carbo-isopropoxy-S-methylisothioureido)-4-propylthiobenzene;
1-iminophenylmethyl-2-(3-carbobutoxy-S-allylisothioureido)-4-phenylthiobenzene;
3-iminophenylmethyl-4-[3-carbo-(2-methoxy)ethoxy-S-methylisothioureido]benzophenone;
1-iminophenylmethyl-2-[3-carbo-(2-methoxy)ethoxy-S-methylisothioureido]-4-propylthiobenzene;
3-iminophenylmethyl-4-(3-carbomethoxy-S-methylisothioureido)-4'-chlorobenzophenone;
3-imino-(p-chlorophenyl)methyl-4-(3-carbomethoxy-S-allylisothioureido)-4'-fluorobenzophenone;
3-iminophenylmethyl-4-(3-carbomethoxy-S-butylisothioureido)-4'-methylbenzophenone;
3-iminophenylmethyl-4-(3-carbomethoxy-S-benzylisothioureido)-4'-methoxybenzophenone;
3-imino-(o-chloro)phenylmethyl-4-(3-carbomethoxy-S-methylisothioureido)-3'-trifluoromethylbenzophenone;
3-iminophenylmethyl-4-(3-carbomethoxy-S-methylisothioureido)propiophenone;
3-iminophenylmethyl-4-(3-carbomethoxy-S-allylisothioureido)-butyrophenone;
3-imino-p-nitrophenylmethyl-4-(3-carbomethoxy-S-butylisothioureido)valerophenone;
1-cyclopropylcarbonyl-3-iminophenylmethyl-4-(3-carbomethoxy-S-methylisothioureido)benzene;
1-cyclopentylcarbonyl-3-imino-(p-chloro)phenylmethyl-4-(3-carbomethoxy-S-butylisothioureido)benzene;
1-(2-theonyl)-3-imino-(p-methyl)phenylmethyl-4-(3-carbomethoxy-S-methylisothioureido)benzene;
1-iminophenylmethyl-2-(3-carbomethoxy-S-methylisothioureido)-4-(4-cyanophenylthio)benzene;
1-iminophenylmethyl-2-(3-carbomethoxy-S-butylisothioureido)-4-(3-cyanophenylthio)benzene;
1-iminophenylmethyl-2-(3-carbomethoxy-S-butylisothioureido)-4-(4-methylthiophenylthio)benzene;
1-iminophenylmethyl-2-(3-carbomethoxy-S-methylisothioureido)-4-(3-methylthiophenylthio)benzene;
1-imino-(p-chlorophenyl)methyl-2-(3-carbomethoxy-S-methylisothioureido)-4-(4-acetylphenylthio)benzene;
1-imino-(p-chlorophenyl)methyl-2-(3-carbomethoxy-S-allylisothioureido)-4-(4-methoxycarbonylphenylthio)benzene;
1-iminophenylmethyl-2-(3-carbomethoxy-S-methylisothioureido)-4-(4-acetylaminophenyl)benzene;
1-iminophenylmethyl-2-(3-carbomethoxy-S-butylisothioureido)-4-(4-phenoxyphenylthio)benzene;
1-iminophenylmethyl-2-(3-carbomethoxy-S-methylisothioureido)-4-(4-cyanophenylsulfinyl)benzene;
1-imino-(p-chlorophenyl)methyl-2-(3-carbomethoxy-S-butylisothioureido)-4-(4-acetylphenylsulfinyl)benzene;
1-iminophenylmethyl-2-(3-carbomethoxy-S-methylisothioureido)-4-(4-cyanophenylsulfonyl)benzene;
1-imino-(p-chlorophenyl)methyl-2-(3-carbomethoxy-S-methylisothioureido)-4-(4-acetylphenylsulfonyl)benzene;
1-imino-(p-chlorophenyl)methyl-2-(3-carbomethoxy-S-methylisothioureido)-4-(4-acetylphenylsulfinyl)benzene;
1-imino-(p-chlorophenyl)methyl-2-(3-carbomethoxy-S-methylisothioureido)-4-(phenylsulfonyl)benzene;
1-imino-(p-chlorophenyl)methyl-2 (3-carbomethoxy-S-methylisothioureido)-5-(4-acetylphenylsulfonyl)benzene;
1-imino-(o-chlorophenyl)methyl-2-(3-carbomethoxy-S-methylisothioureido-5-(4-cyanophenylsulfonyl)benzene;
1-iminophenylmethyl-2-(3-carbomethoxy-S-methylisothioureido)-5-(4-acetylphenylsulfinyl)benzene;
1-iminophenylmethyl-2-(3-carbomethoxy-S-methylisothioureido)-5-(4-cyanophenylsulfinyl)benzene;
1-iminophenylmethyl-2-(3-carbomethoxy-S-methylisothioureido)-5-phenoxysulfonylbenzene;
1-(imino-p-chlorophenylmethyl)-2-(3-carbomethoxy-S-methylisothioureido)-5-(p-chlorophenoxysulfonyl)benzene;
1-(imino-p-chlorophenylmethyl)-2-(3-carbomethoxy-S-butylisothioureido-5-(3-chlorophenoxysulfonyl)benzene;
1-iminophenylmethyl-2-(3-carbomethoxy-S-benzylisothioureido-5-(2 chlorophenoxysulfonyl)benzene;
1-(imino-o-chlorophenylmethyl)-2-(3-carbomethoxy-S-allylisothiouredio)-5-(3,5-dichlorophenoxysulfonyl)benzene;
1-(imino-p-nitrophenylmethyl)-2-(3 carbomethoxy-S-methylisothioureido)-5-(4-methoxyphenoxysulfonyl)benzene;
1-(imino-p-methoxyphenyl)-2-(3-carbomethoxy-S-methylisothioureido)-5-(3-cyanophenoxysulfonyl)benzene;
1-iminophenyl-2-(3-carbomethoxy-S-methylisothioureido)-5-(3-trifluoromethylphenoxysulfonyl)benzene;
1-iminophenylmethyl-2-(3-carbomethoxy-S-methylisothioureido)-5-phenylsulfonyloxybenzene;
1-imino-(p-chlorophenyl)methyl-2-(3-carbomethoxy-S-allylisothioureido)-5-(4-chlorophenyl)sulfonyloxybenzene;
1-imino-(o-chlorophenyl)methyl-2-(3-carbomethoxy-S-butylisothioureido)-5-(3-chlorophenyl)sulfonyloxybenzene;
1-iminophenylmethyl-2-(3-carbomethoxy-S-butylisothioureido)-5-(3,5-dichlorophenyl)sulfonyloxybenzene;
1-imino-(p-nitrophenyl)methyl-2-(3-carbomethoxy-S-benzylisothioureido)-5-(4-methylphenyl)sulfonyloxybenzene;
1-imino-(p-methoxyphenyl)methyl-2-(3-carbomethoxy-S-allylisothioureido)-5-(3-trifluoromethylphenyl)sulfonyloxybenzene;
1-iminophenylmethyl-2-(3-carbomethoxy-S-methylisothioreido)-5-(4-methoxyphenyl)sulfonyloxybenzene.

Examples of other X substituents on known diamines include 4- and 5-propoxy; 4- and 5-phenoxy; 4-and 5-(pyrid-2-yloxy); 4-(4-chlorophenoxy); 4-(trifluoromethylphenoxy); 5-(3-chloropropoxy); 5-(2-phenylethoxy); 5-(3-phenylprop-2-en-1-yloxy); 5-(4-methylphenoxy); 5-(3-methylphenoxy); 5-(2-methylphenoxy); 5-(3-methylthiophenoxy); 5-(propargylthio); 5-(but-3-en-1-yl-thio); 5-(but-3-en-1-yl-sulfinyl); 5-(but-3-en-1-yl-sulfonyl); 5-(benzylthio); 5-(benzylsulfinyl); 5-(thiazol-2-yl-thio); 5-(pyrid-2-yl-thio); 4-pyrimidin-2-yl-thio); 5-(thien-2-yl-thio); 5-(fur-2-yl-thio); 5-(3-chloropropylthio); 4-(3-chloropropylthio); 4-(3-chloroprop-2-en-1-yl-thio); 4-(2-cyanoethylthio); 5-(2,3-dichloropropyl-2-en-1-yl-thio) and the like.

These diamine precursors can be found in U.S. Pat. Nos. 3,657,267; 3,929,823; 3,929,824; 3,935,209; 3,984,561; 3,993,768; 3,996,368; 3,996,369; 4,002,640; French Pat. Nos. 2,248,037; 2,270,861 and Netherlands Pat. No. 4,701,797. These patents, insofar as they are related to the disclosure of the diaminobenzene precursors, are hereby incorporated by reference.

What is claimed is:

1. A compound of the formula:

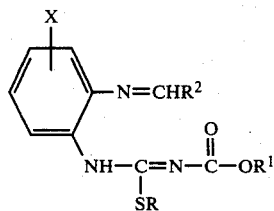

wherein

R is alkyl, alkenyl, alkynyl, polynuclear aralkyl, mononuclear aralkyl, mononuclear aryloxy lower alkyl, cycloalkylalkyl, cyano lower alkyl, hydroxy lower alkyl, aralkenyl, alkoxylakyl, alkoxycarbonylalkyl, phthalimido lower alkyl or phenoxycarbonylalkyl;

$R^1$ is alkyl or lower alkoxyalkyl;

$R^2$ is alkyl or substituted or unsubstituted mononuclear aryl of from 4 to 6 nuclear carbon atoms, polynuclear aryl of from 10 to 14 carbon atoms and heteroaryl of from 5 to 6 nuclear atoms containing from 1 to 3 heteroatoms selected from oxygen, nitrogen or sulfur where the substituent is selected from halo, lower alkyl, lower alkoxy, dilower alkyl amino, lower alkanoylamino, phenoxy, benzyloxy, 3,4-lower alkylenedioxyphenyl, phenylthio lower alkyl, cyano, nitro, alkylthio or phenylthio and X is hydrogen, nitro, halo, lower alkoxy, lower alkanoyl, lower alkyl, thiocyanato, a radical of the formula: Y—S(O)n wherein Y is lower alkyl, lower alkenyl, cyclo lower alkyl, pyridyl, thienyl, furyl, pyrimidyl, thiazolyl or phenyl and n is an integer of 0 to 3, X is also lower alkyl carbonylamino, lower alkoxy carbonylamino, cycloalkylcarbonylamino, a radical of the formula:

wherein Y' is phenyl, cyclo lower alkyl, pyridyl, 2-thienyl or furyl, a radical of the formula: Y"O wherein Y" is lower alkyl, lower alkenyl, mononuclear aralkyl, pyridyl, 2-thienyl or furyl and the nontoxic, pharmaceutically acceptable acid addition salts and amides.

2. A compound according to claim 1 of the formula:

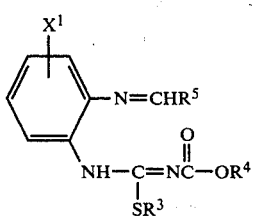

wherein $R^3$ is lower alkyl, lower alkenyl, lower alkynyl, benzyl, 2,6-dichlorobenzyl, phenethyl, cycloalkyl lower alkyl, phenoxy lower alkyl, cyano lower alkyl, lower alkoxy carbonyl lower alkyl, phthalimido lower alkyl, phenyl lower alkenyl or hydroxy lower alkyl;

$R^4$ is lower alkyl;

$R^5$ is mononuclear aryl of from 4 to 6 nuclear carbon atoms, polynuclear aryl of from 10 to 14 nuclear carbon atoms or heteroaryl of from 5 to 6 nuclear atoms containing from 1 to 3 hetero atoms and $X^1$ is hydrogen, lower alkyl carbonylamino, lower alkoxy carbonylamino, lower alkoxy, propylthio, propoxysulfonyl, propylsulfonyloxy, propylsulfinyl, propylsulfonyl, phenylthio, phenylsulfinyl, phenylsulfonyl, phenoxysulfonyl, phenylsulfonyloxy, lower alkanoyl or benzoyl.

3. The compound of claim 2 wherein $R^5$ is nitrophenyl dimethylaminophenyl, lower alkoxyphenyl, cyanophenyl, acetamidophenyl, methylenedioxyphenyl, phenyl, halophenyl, furyl, thienyl, lower alkyl phenyl or dihalophenyl.

4. The compound of claim 3 wherein $X^1$ is hydrogen, 4-benzoyl, 5-propylthio or 5-phenylthio.

5. The compound according to claim 4 named 3-imino-phenylmethyl-4-(3-carbomethoxy-S-methylisothioureido)-benzophenone.

6. The compound according to claim 4 named 3-imino-(4-chlorophenyl)methyl-4-(3-carbomethoxy-S-methylisothioureido)benzophenone.

7. The compound according to claim 4 named 1-iminophenylmethyl-2-(3-carbomethoxy-S-methylisothioureido)-4-propylthiobenzene.

8. The compound according to claim 4 named 1-imino-(4-chlorophenyl)methyl-2-(3-carbomethoxy-S-methylisothioureido)-4-phenylthiobenzene.

9. The compound according to claim 4 named 1-imino-(4-chlorophenyl)methyl-2-(3-carbomethoxy-S-methylisothioureido)-4-propylthiobenzene.

10. The compound according to claim 4 named 1-imino-(2-furylmethyl)-2-(3-carbomethoxy-S-benzylisothioureido)-benzene.

11. The compound according to claim 4 named 1-imino-(2-furylmethyl)-2-(3-carbomethoxy-S-butylisothioureido)-benzene.

12. The compound according to claim 4 named 1-imino-(2-furylmethyl)2-(3-carbomethoxy-S-methylisothioureido)-benzene.

13. A composition useful in the treatment of helminths which comprises a dosage of between about 1 milligram per kilogram and about 125 milligrams per kilograms of body weight of a compound of claim 1 in a pharmaceutically carrier.

14. A composition useful in the treatment of helminths which comprises a unit dosage between about 1 milligram per kilogram and about 125 milligrams per kilograms of body weight of a compound of claim 2 in a pharmaceutically carrier.

15. A composition useful in the treatment of helminths which comprises a unit dosage between about 1 milligram per kilogram and about 125 milligrams per kilogram of body weight of the compound of claim 3 in a pharmaceutically carrier.

16. A composition useful in the treatment of helminths which comprises the unit dosage between about 1 milligram per kilogram and 125 milligrams per kilograms of body weight of the compound of claim 4 in a pharmaceutically acceptable carrier.

17. A composition useful in the treatment of helminths which comprises the unit dosage between about 1 milligram per kilogram and 125 milligrams per kilograms of body weight of the compound of claim 5 in a pharmaceutically acceptable carrier.

18. A composition useful in the treatment of helminths which comprises the unit dosage between about 1 milligram per kilogram and 125 milligrams per kilograms of body weight of the compound of claim 6 in a pharmaceutically acceptable carrier.

19. A composition useful in the treatment of helminths which comprises the unit dosage between about 1 milligram per kilogram and 125 milligrams per kilograms of body weight of the compound of claim 7 in a pharmaceutically acceptable carrier.

20. A composition useful in the treatment of helminths which comprises the unit dosage between about 1 milligram per kilogram and 125 milligrams per kilograms of body weight of the compound of claim 8 in a pharmaceutically acceptable carrier.

21. A composition useful in the treatment of helminths which comprises the unit dosage between about 1 milligram per kilogram and 125 milligrams per kilograms of body weight of the compound of claim 9 in a pharmaceutically acceptable carrier.

22. A composition useful in the treatment of helminths which comprises the unit dosage between about 1 milligram per kilogram and 125 milligrams per kilograms of body weight of the compound of claim 10 in a pharmaceutically acceptable carrier.

23. A composition useful in the treatment of helminths which comprises the unit dosage between about 1 milligram per kilogram and 125 milligrams per kilograms of body weight of the compound of claim 11 in a pharmaceutically acceptable carrier.

24. A composition useful in the treatment of helminths which comprises the unit dosage between about 1 milligram per kilogram and 125 milligrams per kilograms of body weight of the compound of claim 12 in a pharmaceutically acceptable carrier.

25. A method for treating helminths and fungal infections which comprises the administration of an effective amount of the compound of claim 1.

26. A method for treating helminths and fungal infections which comprises the administration of an effective amount of the compound of claim 2.

27. A method for treating helminths and fungal infections which comprises the administration of an effective amount of the compound of claim 3.

28. A method for treating helminths and fungal infections which comprises the administration of an effective amount of the compound of claim 4.

29. A method for treating helminths and fungal infections which comprises the administration of an effective amount of the compound of claim 5.

30. A method for treating helminths and fungal infections which comprises the administration of an effective amount of the compound of claim 6.

31. A method for treating helminths and fungal infections which comprises the administration of an effective amount of the compound of claim 7.

32. A method for treating helminths and fungal infections which comprises the administration of an effective amount of the compound of claim 8.

33. A method for treating helminths and fungal infections which comprises the administration of an effective amount of the compound of claim 9.

34. A method for treating helminths and fungal infections which comprises the administration of an effective amount of the compound of claim 10.

35. A method for treating helminths and fungal infections which comprises the administration of an effective amount of the compound of claim 11.

36. A method for treating helminths and fungal infections which comprises the administration of an effective amount of the compound of claim 12.

37. A composition useful as a need protectant, soil fungicide or foliar fungicide which comprises from about 0.1 to about 20 oz per 100 lbs. of seed, from about 0.1 to about 50 lbs. per acre and from about 0.25 to about 10 lbs. per acre, respectively of the compound of claim 1 in an agronomically acceptable carrier.

38. The composition of claim 37 useful as a seed protectant, soil fungicide or foliar fungicide which comprises from about 0.1 to about 20 ozs. per 10 lbs. of seed, from about 0.1 to about 50 lbs. per acre and from about 0.25 to about 10 lbs. per acre, respectively, of the compound of claim 2 in an agronomically acceptable carrier.

39. The composition according to claim 37 which comprises from 0.1 to about 20 ozs. per 10 lbs. of seed, from about 0.1 to about 50 lbs. per acre and from about 0.25 to about 10 lbs. per acre, respectively, of the compound of claim 3 in an agronomically acceptable carrier.

40. The composition according to claim 37 which comprises from 0.1 to about 20 ozs. per 10 lbs. of seed, from about 0.1 to about 50 lbs. per acre and from about 0.25 to about 10 lbs. per acre, respectively, of the compound of claim 9 in an agronomically acceptable carrier.

41. The composition according to claim 37 which comprises from about 0.1 to about 20 ozs. per 10 lbs. of seed, from about 0.1 to about 50 lbs. per acre and from about 0.25 to about 10 lbs. per acre, respectively, of the compound of claim 10 in an agronomically acceptable carrier.

42. The composition according to claim 37 which comprises from about 0.1 to about 20 ozs. per 10 lbs. of seed, from about 0.1 to about 50 lbs. per acre and from about 0.25 to about 10 lbs. per acre of the compound of claim 11 in an agronomically acceptable carrier.

43. The composition according to claim 37 which comprises from about 20 ozs. per 10 lbs. of seed, from about 0.1 to about 50 lbs. per acre and from about 0.25 to about 10 lbs. per acre of the compound of claim 12 in an agronomically acceptable carrier.

44. A method for treating fungi which comprises the administration of an effective amount of a compound having the formula:

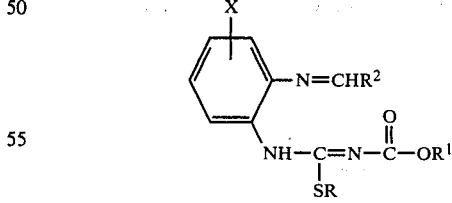

wherein
R is alkyl, alkenyl, alkynyl, polynuclear aralkyl, mononuclear aralkyl, mononuclear aryloxy lower alkyl, cycloalkylalkyl, cyano lower alkyl, hydroxy lower alkyl, aralkenyl, alkoxyalkyl, alkoxycarbonylalkyl, phthalimido lower alkyl or phenoxycarbonylalkyl;
$R^1$ is lower or lower alkyl;
$R^2$ is alkyl or substituted or unsubstituted mononuclear aryl of from 4 to 6 nuclear carbon atoms, polynuclear aryl of from 10 to 14 carbon atoms or heteroaryl of from 5 to 6 nuclear atoms containing from 1 to 3 heteroatoms where the substituent is selected from halo, lower alkyl, lower alkoxy, di-lower alkyl amino lower alkanoylamino, phenoxy, benzyloxy, 3,4-lower alkylenedioxyphenyl, phenylthio lower alkyl, cyano, nitro, alkylthio or phenylthio and X is hydrogen, nitro, halo, lower alkanoyl, lower alkyl, lower alkoxy, thiocyanato, a radical of the formula: Y—S(O)n wherein Y is lower alkyl, lower alkenyl, cyclo lower alkyl, pyridyl, thienyl, furyl, pyrimidyl, thiazolyl or phenyl and n is an integer of 0 to 3; X is also lower alkylcarbonylamino, lower alkoxycarbonylamino, cycloalkylcarbonylamino, a radical of the formula:

where Y' is pyenyl, cyclo lower alkyl, pyridyl, 2-thienyl or furyl, a radical of the formula: Y"O wherein Y" is lower alkyl, lower alkenyl, phenyl, mononuclear aralkyl or pyridyl, 2-thienyl or furyl and the nontoxic, pharmaceutically acceptable acid addition salts and amides.

45. The method of claim 44 wherein the compound has the formula:

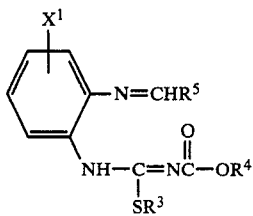

wherein $R^3$ is lower alkyl, lower alkenyl, lower alkynyl, benzyl, 2,6-dichlorobenzyl, phenethyl, cycloalkyl lower alkyl, phenoxy lower alkyl, cyano lower alkyl, lower alkoxy carbonyl lower alkyl, phthalimido lower alkyl, phenyl lower alkenyl or hydroxy lower alkyl;

$R^4$ is lower alkyl;

$R^5$ is mononuclear aryl of from 4 to 6 nuclear carbon atoms, polynuclear aryl of from 10 to 14 nuclear carbon atoms in heteroaryl of from 5 to 6 nuclear atoms containing from 1 to 3 hetero atoms and $X^1$ is hydrogen, lower alkyl carbonylamino, lower alkoxy carbonylamino, lower alkoxy, propylthio, propoxysulfonyl, propylsulfonyloxy, propylsulfinyl, propylsulfonyl, phenylthio, phenylsulfinyl, phenylsulfonyl, phenoxysulfonyl, phenylsulfonyloxy, lower alkanoyl or benzoyl.

46. The method of claim 45 wherein $R^5$ is nitrophenyl, dimethylaminophenyl, lower alkoxyphenyl, cyanophenyl, acetamidophenyl, methylenedioxyphenyl, phenyl, halophenyl, furyl, thienyl, lower alkyl phenyl or dihalophenyl.

47. The method of claim 46 wherein $X^1$ is hydrogen, 4-benzoyl, 5-propylthio or 5-phenylthio.

48. The method of claim 47 wherein the compound is 1-imino-(2-furylmethyl)-2-(3-carbomethoxy-S-benzylisothioureido)-benzene.

49. The method of claim 47 wherein the compound is 1-imino-(2-furylmethyl)-2-(3-carbomethoxy-S-butylisothioureido)-benzene.

50. The method of claim 47 wherein the compound is 1-imino-(2-furylmethyl)2-(3-carbomethoxy-S-methylisothioureido)-benzene.

* * * * *